(12) United States Patent
Lebrija et al.

(10) Patent No.: US 11,547,425 B1
(45) Date of Patent: Jan. 10, 2023

(54) TARSOMETATARSAL JOINT ARTHRODESIS TOOLS AND RELATED METHOD FOR BUNION CORRECTION

(71) Applicant: Gramercy Extremity Orthopedics LLC, Richardson, TX (US)

(72) Inventors: Edward A. Lebrija, Richardson, TX (US); Paul J. Vasta, Richardson, TX (US); Scott Campbell, Richardson, TX (US)

(73) Assignee: GRAMERCY EXTREMITY ORTHOPEDICS LLC, Richardson, TX (US)

( * ) Notice: Subject to any disclaimer, the term of this patent is extended or adjusted under 35 U.S.C. 154(b) by 0 days.

(21) Appl. No.: 17/870,300

(22) Filed: Jul. 21, 2022

Related U.S. Application Data

(60) Provisional application No. 63/343,566, filed on May 19, 2022.

(51) Int. Cl.
*A61B 17/17* (2006.01)
*A61B 17/15* (2006.01)
*A61B 17/56* (2006.01)

(52) U.S. Cl.
CPC ........ *A61B 17/1775* (2016.11); *A61B 17/152* (2013.01); *A61B 17/17* (2013.01); *A61B 17/1739* (2013.01); *A61B 2017/565* (2013.01)

(58) Field of Classification Search
CPC .............. A61B 17/1775; A61B 17/152; A61B 17/1739; A61B 17/17
See application file for complete search history.

(56) References Cited

U.S. PATENT DOCUMENTS

| 4,729,369 | A | 3/1988 | Cook |
|---|---|---|---|
| 5,042,983 | A | 8/1991 | Rayhack |
| 5,176,685 | A | 1/1993 | Rayhack |
| 6,007,535 | A | 12/1999 | Rayhack et al. |
| 6,629,943 | B1 | 10/2003 | Schroder |
| 8,282,645 | B2 | 10/2012 | Lawrence et al. |
| 8,753,348 | B2 | 6/2014 | DiDomenico et al. |
| 9,622,805 | B2 | 4/2017 | Santrock et al. |
| 9,687,250 | B2 | 6/2017 | Dayton et al. |

(Continued)

FOREIGN PATENT DOCUMENTS

GB 2589960 A 6/2021

*Primary Examiner* — Christian A Sevilla
(74) *Attorney, Agent, or Firm* — Panitch Schwarze Belisario & Nadel LLP

(57) ABSTRACT

A kit of tarsometatarsal joint arthrodesis tools include a metatarsal multi-tool, a first ray multi-tool, a cuneiform cut guide, and a joint compressor-distractor. The metatarsal multi-tool is configured for securement to a first metatarsal establishing an anatomic reference for carrying out a surgical procedure and guiding a surgeon to perform the metatarsal base cut. The first ray multi-tool is configured for securement to the first metatarsal using a fixation method. The first ray multi-tool is also configured to be secured to the medial cuneiform. The cuneiform cut guide is configured for removable attachment to the first ray multi-tool and is configured to guide the surgeon to perform the cuneiform head cut. The compressor-distractor is configured to apply a force to the first ray multi-tool such that the position of the first metatarsal may be adjusted toward or away from the medial cuneiform.

19 Claims, 18 Drawing Sheets

(56) References Cited

U.S. PATENT DOCUMENTS

| | | | |
|---|---|---|---|
| 9,936,994 B2 | 4/2018 | Smith et al. | |
| 10,045,807 B2 | 8/2018 | Santrock et al. | |
| 10,245,088 B2 | 4/2019 | Dayton et al. | |
| 10,292,713 B2 | 5/2019 | Fallin et al. | |
| 10,335,220 B2 | 7/2019 | Smith et al. | |
| 10,342,590 B2* | 7/2019 | Bays | A61B 17/1728 |
| 10,470,779 B2 | 11/2019 | Fallin et al. | |
| 10,512,470 B1 | 12/2019 | Bays et al. | |
| 10,524,808 B1* | 1/2020 | Hissong | A61B 17/1775 |
| 10,555,757 B2 | 2/2020 | Dayton | |
| 10,561,426 B1 | 2/2020 | Dayton et al. | |
| 10,575,862 B2 | 3/2020 | Bays et al. | |
| 10,582,936 B1 | 3/2020 | Hissong et al. | |
| 10,603,046 B2 | 3/2020 | Dayton et al. | |
| 10,610,241 B2 | 4/2020 | Wagner et al. | |
| 10,646,263 B2 | 5/2020 | Lamm et al. | |
| 10,743,995 B2 | 8/2020 | Fallin et al. | |
| 10,849,631 B2 | 12/2020 | Hatch et al. | |
| 10,849,663 B2 | 12/2020 | Dayton et al. | |
| 10,849,670 B2 | 12/2020 | Santrock et al. | |
| 10,874,446 B2 | 12/2020 | Smith et al. | |
| 10,888,335 B2 | 1/2021 | Dayton et al. | |
| 10,939,939 B1 | 3/2021 | Gil et al. | |
| 10,945,764 B2 | 3/2021 | Dayton et al. | |
| 11,020,148 B2 | 6/2021 | Hollis et al. | |
| 11,039,873 B2 | 6/2021 | Santrock et al. | |
| 11,076,863 B1 | 8/2021 | Bays et al. | |
| 11,116,558 B2 | 9/2021 | Smith et al. | |
| 11,147,590 B2 | 10/2021 | Dayton et al. | |
| 11,154,340 B2 | 10/2021 | Dayton et al. | |
| 11,185,359 B2 | 11/2021 | Smith et al. | |
| 11,213,333 B2 | 1/2022 | Santrock et al. | |
| 11,224,469 B2 | 1/2022 | Schumacher et al. | |
| 11,278,337 B2 | 3/2022 | Bays et al. | |
| 11,304,705 B2 | 4/2022 | Fallin et al. | |
| 11,304,735 B2 | 4/2022 | Sayger et al. | |
| 11,344,347 B2 | 5/2022 | Treace et al. | |
| 11,389,221 B2* | 7/2022 | Tyber | A61B 17/68 |
| 2008/0039850 A1 | 2/2008 | Rowley et al. | |
| 2012/0016428 A1 | 1/2012 | White et al. | |
| 2016/0213384 A1* | 7/2016 | Fallin | A61B 17/151 |
| 2017/0014143 A1 | 1/2017 | Dayton et al. | |
| 2017/0042598 A1 | 2/2017 | Santrock et al. | |
| 2020/0015856 A1 | 1/2020 | Treace et al. | |
| 2020/0155176 A1 | 5/2020 | Bays et al. | |
| 2020/0253641 A1* | 8/2020 | Treace | A61B 17/56 |
| 2021/0038212 A1 | 2/2021 | May et al. | |
| 2021/0077120 A1 | 3/2021 | Hatch et al. | |
| 2021/0077131 A1 | 3/2021 | Denham et al. | |
| 2021/0093328 A1 | 4/2021 | Dayton et al. | |
| 2021/0161246 A1 | 6/2021 | Lesser | |
| 2021/0196324 A1 | 7/2021 | Dayton et al. | |
| 2021/0251670 A1 | 8/2021 | Sayger et al. | |
| 2021/0290250 A1 | 9/2021 | Denham et al. | |
| 2021/0330311 A1 | 10/2021 | Denham et al. | |
| 2021/0338450 A1 | 11/2021 | Hollis et al. | |
| 2021/0369287 A1* | 12/2021 | Boffeli | A61B 17/8095 |
| 2022/0151645 A1* | 5/2022 | Cundiff | A61B 17/025 |

\* cited by examiner

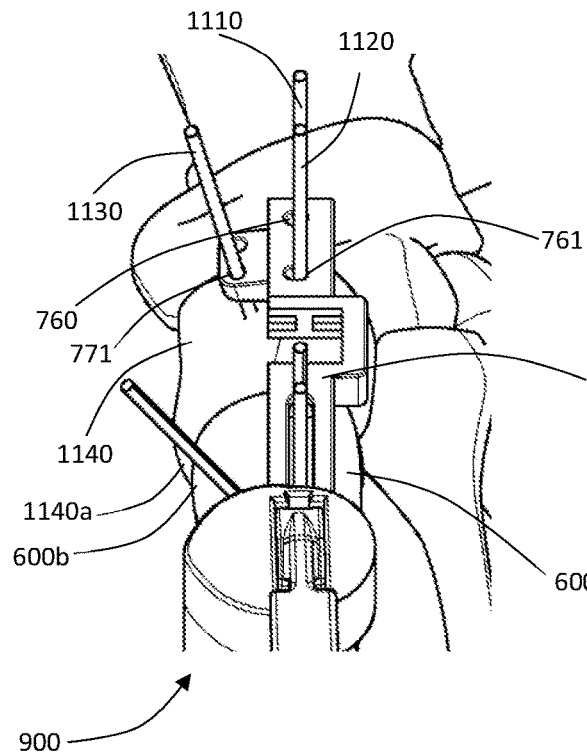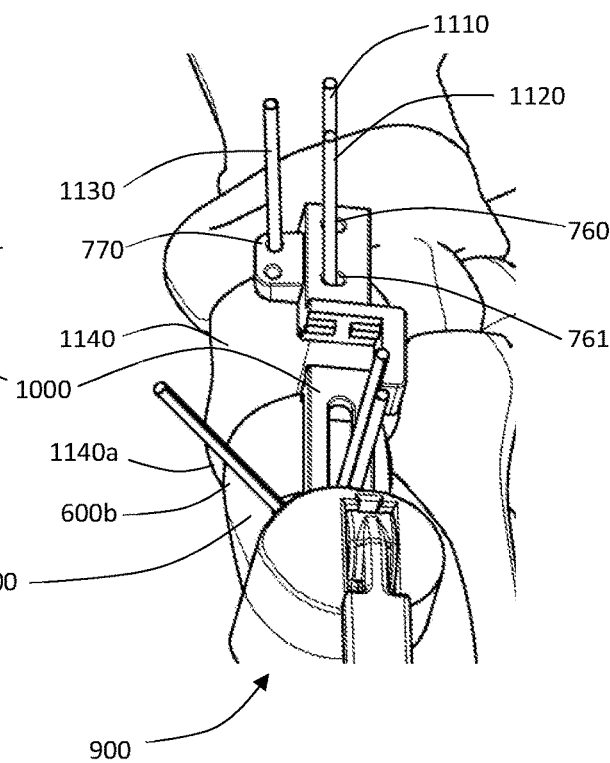
Fig. 12a
Fig. 12b
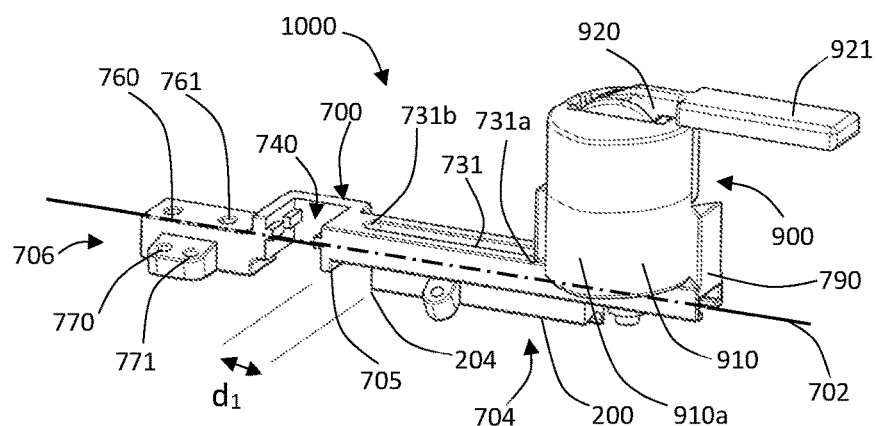
Fig. 13

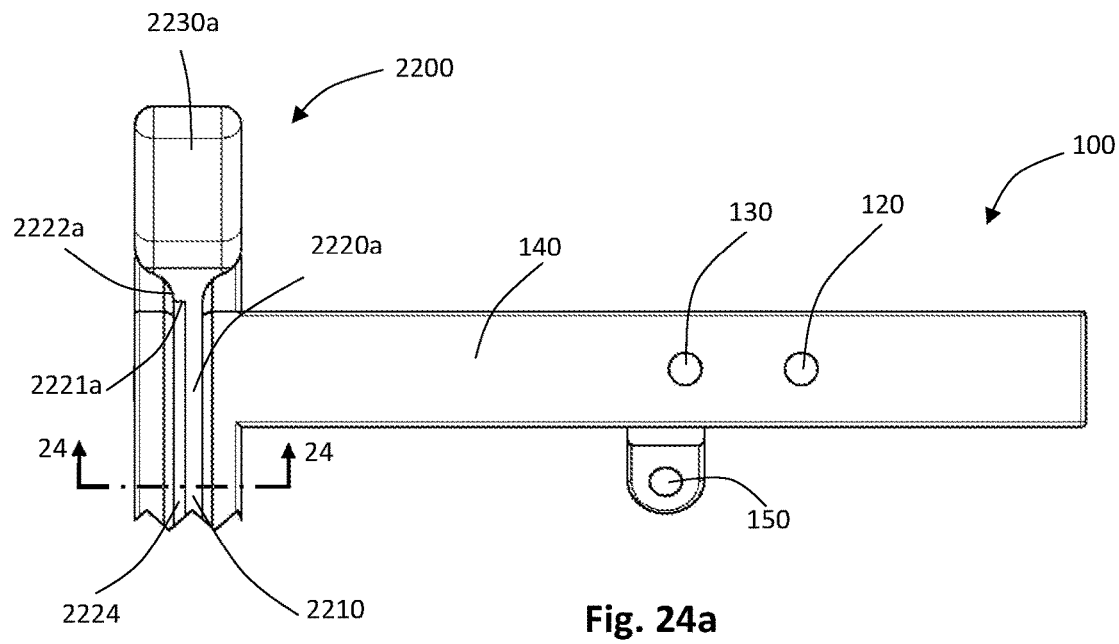
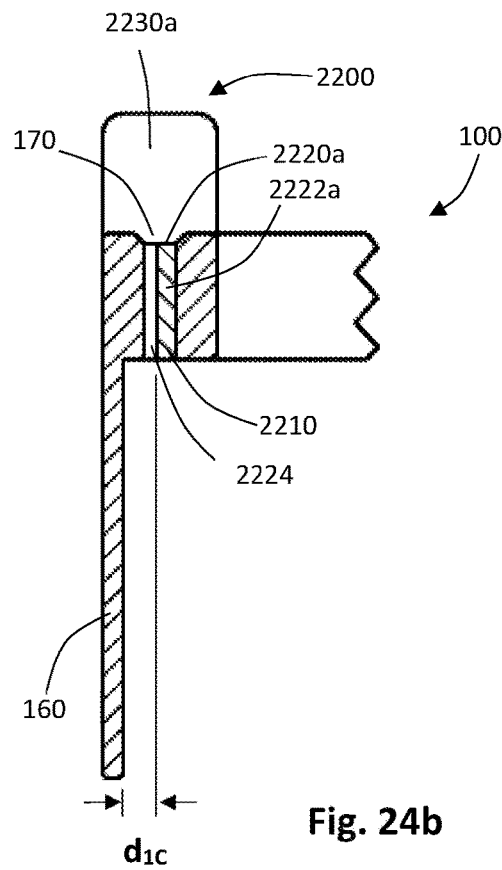
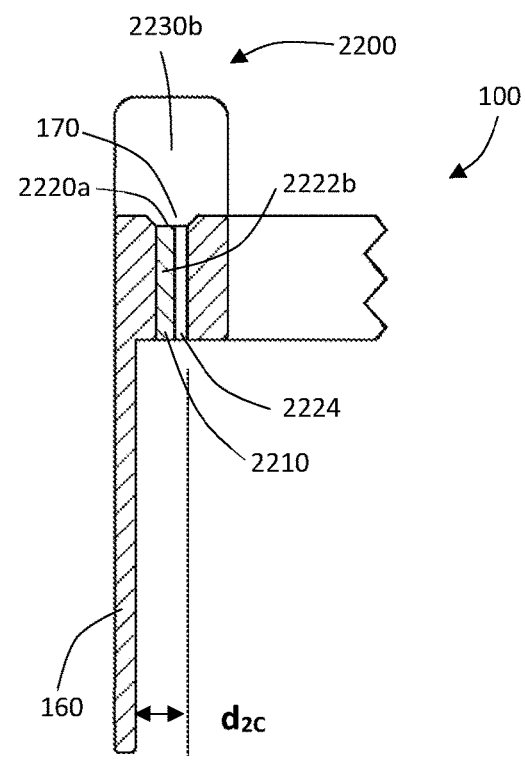

TARSOMETATARSAL JOINT ARTHRODESIS TOOLS AND RELATED METHOD FOR BUNION CORRECTION

CROSS-REFERENCE TO RELATED APPLICATIONS

The present application claims the benefit of U.S. Provisional Patent Application No. 63/343,566, filed May 19, 2022 and titled, "Tarsometatarsal Joint Arthrodesis Tools and related Method for Bunion Correction," the entire contents of which is incorporated herein by reference in its entirety.

BACKGROUND OF THE INVENTION

Bunion correction surgery is a common procedure performed to re-align the first metatarsal from a deformed position, indicated by increased mobility of the first ray, medial deviation of the distal end of the first metatarsal, and rotation about its long axis. The condition is referred to as hallux (abducto) valgus deformity and is widely considered to be caused by hypermobility of the tarsometatarsal joint, however some consider hypermobility to be the result of the deformity. Surgical intervention can be performed at the proximal or distal ends of the first metatarsal, depending on the severity of the condition and surgeon preference. Where there is extensive first ray mobility, deformity, pain, or recurrence from a previous surgical intervention, fusion of the tarsometatarsal ("TMT") joint is typically performed. This procedure is commonly referred to as the Lapidus procedure, named in honor of Paul W. Lapidus who popularized the approach.

The Lapidus bunion correction procedure has evolved over the many years since it was introduced in the early part of the Twentieth century. Initially correction was a simple linear realignment of the first metatarsal generally in the transverse plane, however modern thinking considers Lapidus bunion correction to be tri-planar, including corrections in the transverse, sagittal, and frontal planes, the latter corresponding to rotation about the long axis of the metatarsal. Subsequently, the multidimensional corrective manipulation of the first metatarsal has increased the complexity of the surgical procedure, requiring both the ability to spatially visualize the corrective realignment and perform a more intricate surgical procedure.

The additional burden on the surgeon to perform the modern version of the Lapidus procedure is considered to have limited the frequency of which the procedure was performed, leaving fewer surgeons to perform the surgery. Correspondingly, additional pressure from patients for quicker recovery and less scarring has increased the preference of a more robust yet minimally invasive approach. In an attempt to facilitate execution of the Lapidus procedure, device manufacturers have devised various surgical tools to aid in one or more of the multi-planar correction maneuvers as well as TMT joint preparation. However, the underlying complexity of the procedure has resulted in such instrument systems incorporating a multitude of components and/or many procedural steps in order to carry out the correction. While improvements of Lapidus procedure instruments have been made over time, there remains a gap in the current offerings that is simple, has few components, a small number of surgical steps, and reduces the overall complexity of the Lapidus procedure.

BRIEF SUMMARY OF THE INVENTION

In a first aspect, the preferred present invention relates to a set of tarsometatarsal joint arthrodesis tools that may include a metatarsal multi-tool, a first ray multi-tool, a cuneiform cut guide, and a joint compressor-distractor. The tools may be comprised of a delivered to a user in a kit that is preferably comprised of at least two tools or components but may include more tools and components, for example, the metatarsal multi-tool, first ray multi-tool, cuneiform cut guide, joint compressor-distractor, fasteners, bone pins, saws and other instruments or tools. The metatarsal multi-tool is configured to be secured to a first metatarsal, establishing both an anatomic reference for carrying out a surgical procedure to correct a bunion deformity using the remaining components of the instrument set and guiding a surgeon to perform the metatarsal base cut. The first ray multi-tool is configured to be secured to the first metatarsal using the same fixation method as established for the metatarsal multi-tool, thereby retaining the same positioning. The first ray multi-tool is also configured to be secured to the medial cuneiform. The cuneiform cut guide is configured to be removably attached to the first ray multi-tool and is configured to guide the surgeon to perform the cuneiform head cut. The compressor-distractor is configured to apply a force to the first ray multi-tool generally along the axis of the first ray such that the position of the first metatarsal may be adjusted toward or away from the medial cuneiform.

In another aspect, the preferred present invention relates to the instrument set of tarsometatarsal joint arthrodesis tools preferably supplied to the user as an instrument kit in a terminally sterilized package. The tools are preferably constructed of biocompatible and relatively strong and stiff metal materials, however one or more of the tools and instruments, including component parts, can be constructed of biocompatible and relatively strong and stiff polymeric or plastic materials or other suitable materials. The tools are preferably single use and disposable after use, although are not so limited and may be designed and configured for sterilization and multiple uses. Individual kits for specific procedures may be supplied to the user in a sterile package or tools and components may be supplied in multiple packages or individually.

In yet another aspect, the preferred present invention relates to a method of performing bunion correction and joint fusion using the tarsometatarsal joint arthrodesis tools. The set of tarsometatarsal joint arthrodesis tools may include a metatarsal multi-tool, a first ray multi-tool, a cuneiform cut guide, and a compressor-distractor, which may be supplied to the user in a sterile package. In operation, the user secures the metatarsal multi-tool onto the first metatarsal in alignment with the first metatarsal anatomy and the metatarsal base. The metatarsal base is cut, and the articular surface is removed, the metatarsal multi-tool is removed and replaced by the first ray multi-tool and secured in the same position on the metatarsal. The attached cuneiform cut guide is placed in alignment with the cuneiform head and the user then corrects the orientation of the first metatarsal. The user secures the first ray alignment guide to the medial cuneiform, the head of the medial cuneiform is cut, and the articular surface is removed. The cuneiform cut guide is removed from the first ray multi-tool and the user then manipulates the compressor-distractor to achieve abutment of the cut first metatarsal base against the cut medial cuneiform head. The joint is secured with standard orthopedic fixation devices and the first ray alignment assembly is removed.

In yet another aspect, the metatarsal multi-tool preferably includes a body portion, a positioner portion, and a cut guide portion. The body portion includes a bone-contact side having a geometry generally mirroring the surface anatomy of the proximal dorsal aspect of the first metatarsal. The bone-contact surface is intended to contact the dorsal aspect of the first metatarsal such that tactile feedback can be communicated to the surgeon upon placing the metatarsal base scaffold in the correct alignment with the bony anatomy of the first metatarsal. The body portion of the metatarsal multi-tool preferably includes holes that can accept bone pins for securing the scaffold to the first metatarsal. Preferably, there are three holes for accepting bone pins, of which the axes of two of the holes are parallel to each other and generally perpendicular to the longitudinal axis of the metatarsal multi-tool, and a third hole with an axis that is at an oblique angle to the axes of the parallel holes. Preferably, the positioner portion extends generally perpendicular to the longitudinal axis of the body portion in a medial direction and a downward direction from the body portion with geometry appropriate for insertion into the TMT joint. The cut guide portion is preferably proximate and proximal to the positioner portion, opposite to the body portion. The cut guide portion includes a slot dimensionally appropriate for insertion of a bone saw, the slot extending medially from the body portion and parallel to the positioner portion.

In yet another aspect, the preferred present invention is directed to a set of tarsometatarsal joint arthrodesis tools having a metatarsal base scaffold separate from a metatarsal base cut guide. The metatarsal base scaffold is configured to include a bone-contact side and an opposite side with features to allow removable attachment of both the metatarsal base cut guide and a first ray alignment guide. The bone-contact side having a geometry generally mirroring the surface anatomy of the proximal dorsal aspect of the first metatarsal. The bone-contact surface is intended to contact the dorsal aspect of the first metatarsal such that tactile feedback can be communicated to the surgeon upon placing the metatarsal base scaffold in the correct alignment with the bony anatomy of the first metatarsal. The side generally opposite to the bone-contact surface preferably includes a threaded hole to accept a threaded locking knob or other means for removably attaching the metatarsal base cut guide. Additionally, the metatarsal base scaffold includes holes that can accept bone pins for securing the scaffold to the first metatarsal. Preferably, there are three holes for accepting bone pins, of which the axes of two of the holes are parallel to each other and generally perpendicular to the longitudinal axis of the metatarsal base scaffold, and a third hole with an axis that is at an oblique angle to the axis of the parallel holes. Preferably the features of the metatarsal base scaffold correspond to either the left or right first metatarsal, however geometry appropriate for use on either left or right anatomy is contemplated.

In yet another aspect, the preferred present invention is directed to a set of tarsometatarsal joint arthrodesis tools having a separate metatarsal base cut guide. The metatarsal base cut guide is attachable to the metatarsal base scaffold and preferably includes a body portion, a metatarsal base positioner portion, and a cut guide portion. Preferably, the body portion includes a hole that accepts the threaded shaft of a locking knob to removably secure the cut guide to the metatarsal base scaffold. The metatarsal base cut guide body portion also includes holes generally aligned with the parallel pin holes of the metatarsal base scaffold. Preferably, the metatarsal base positioner portion extends generally perpendicular to the longitudinal axis of the body portion in a medial direction and a downward direction from the body portion with geometry appropriate for insertion into the TMT joint. The cut guide portion is preferably proximate and proximal to the positioner portion, opposite to the body portion. The cut guide portion includes a slot dimensionally appropriate for insertion of a bone saw, the slot extending medially from the body portion and parallel to the positioner portion. The preferred instrument set of tarsometatarsal joint arthrodesis tools is supplied to the user with the metatarsal base cut guide removably attached to the metatarsal base scaffold. It should be understood that the metatarsal multi-tool supplied to the user in the tarsometatarsal joint arthrodesis tool set is a single piece combination of the metatarsal base scaffold and the metatarsal base cut guide.

In yet another aspect, the preferred present invention is directed to a set of tarsometatarsal joint arthrodesis tools having a separate metatarsal first ray alignment guide. The first ray alignment guide is attachable to the metatarsal base scaffold and preferably includes a cuneiform portion, a cut guide portion, a body portion, and a compression-distraction assembly. Preferably, the body portion includes features for aligning with, and allowing slidable linear motion along, the metatarsal base scaffold. The body portion preferably includes an opening, aperture or slot which allows translation along the longitudinal axis of the metatarsal base scaffold unimpeded by the bone pins or attachment device and includes rail features that correspond with slots in the sides of the metatarsal base scaffold to generally restrict motion in any direction other than the longitudinal axis of the metatarsal base scaffold. The cut guide portion preferably includes receiving guides to removably attach the cuneiform cut guide and allow for unobstructed visibility of the TMT joint space when the cuneiform cut guide is removed. The cuneiform portion preferably is configured to contact the dorsal surface of the medial cuneiform and accept bone pins for attachment thereto to fix the cuneiform portion to the medial cuneiform. The compression-distraction assembly is preferably configured to receive the joint compressor-distractor and includes buttresses, such as posts, pins or other relatively stiff and strong features against which the joint compressor-distractor cam imparts forces. The preferred embodiment of the metatarsal base scaffold includes a receptacle for receiving the preferred embodiment of the compressor-distractor cam axle and the first ray alignment guide compression-distraction portion includes an opening which allows translation along the longitudinal axis of the metatarsal base scaffold generally unimpeded by the joint compressor-distractor. In a preferred embodiment, the first ray alignment guide is translatably attached to the metatarsal base scaffold and is preferably not removable and the joint compressor-distractor assembly is attached to the metatarsal base scaffold through the first ray alignment guide and is preferably not removable. This configuration of the first ray multi-tool may be supplied to the user in the instrument kit. In another preferred embodiment, the first ray alignment guide is supplied to the user in the instrument kit separate from the metatarsal base scaffold and the joint compressor-distractor assembly is supplied to the user in the instrument kit separate from the first ray alignment guide. Alternate removably or permanently attached combinations of the metatarsal base scaffold, first ray alignment guide, and joint compressor-distractor supplied to the user in the instrument kit are contemplated herein. The kit is preferably comprised of at least two components of the tarsometatarsal joint arthrodesis tools and instruments described herein, such as the first metatarsal cut guide and a bone pin packaged in a sterile package, the base scaffold and the cut guide packaged in a sterile package, the base scaffold, first ray alignment guide and compressor-distractor assembly packaged in a sterile package, the base scaffold, comprised of a first base scaffold and a second base scaffold, first ray alignment guide, cut guide and compressor-distractor assembly packaged in a sterile package, or other combinations of tools and instruments, preferably including at least two tools, instruments or components packaged together for supply to the user. The preferred kits described herein are not limited to being packaged together to define the kit or to being packaged in a sterile package. The kit may be comprised of two or more instruments, tools and/or components that are provided to the user to correct a deformity between two or more bones, such as the first metatarsal and medial cuneiform of the patient's foot.

In a further aspect, the preferred present invention includes the first ray alignment guide with holes for receiving bone pins for the purpose of securing the first ray alignment guide to the medial cuneiform. The holes are configured to allow rotation of the first ray alignment guide about the long axis of the first metatarsal after initial alignment of the first metatarsal and fixation to the medial cuneiform and without removal of the bone pins. The bone pin holes include a gradual uni-directional expansion extending from the bone-contact surface to the opposite surface and along a medial-lateral direction. These bone pin holes, slots or apertures with the gradual uni-directional expansion facilitate introduction of the bone pins into the bone pin holes, slots, or apertures and stable fixation of the first ray alignment guide to the associated bone or bone segment.

In a further aspect, the preferred present invention is directed to a method of performing bunion correction and joint fusion with a metatarsal multi-tool, a first ray multi-tool, and a cuneiform cut guide, wherein the metatarsal multi-tool is secured to the dorsal surface of the first metatarsal and the base of the first metatarsal is cut. The metatarsal multi-tool is then replaced by the first ray multi-tool, the first metatarsal is repositioned to a corrected anatomical position, and the first ray multi-tool is secured to the cuneiform with bone pins, wherein two bone pins are secured through two parallel tapered holes on the upper surface of the proximal end of the first ray alignment guide and one bone pin at an oblique angle to the parallel bone pins. The cuneiform head is cut, and the user removes the oblique bone pin and rotates the first metatarsal and attached first ray multi-tool without removing the parallel bone pins. After the first metatarsal rotation, the oblique bone pin is inserted to secure the first ray multi-tool and associated first ray of the foot. Compression-distraction and/or joint fixation is then performed.

In yet another aspect, the preferred present invention is directed to a set of tarsometatarsal joint arthrodesis tools having a cuneiform cut guide configured to be removably attachable to the cut guide portion of the first ray alignment guide. Preferably, the cuneiform cut guide positioner portion extends generally perpendicular to the longitudinal axis of the first ray alignment guide in a medial direction and a downward direction from the first ray alignment guide cut guide portion with geometry appropriate for insertion into the TMT joint. The positioner portion being proximate to the first ray alignment guide cuneiform portion. The cuneiform cut guide portion is preferably proximate and distal to the positioner portion, opposite to the cuneiform alignment guide cuneiform portion. The cut guide portion includes a slot dimensionally appropriate for insertion of a bone saw, the slot extending medially from the body portion and parallel to the positioner portion. The cuneiform cut guide preferably includes an attached alignment outrigger to aid in the positional correction of the first metatarsal in the transverse plane. When attached to the first ray alignment guide, the cuneiform cut guide alignment outrigger extends laterally from the cuneiform cut guide then distally approximately above the second metatarsal in a direction parallel to the longitudinal axis of the first ray alignment guide. The preferred instrument set of tarsometatarsal joint arthrodesis tools is supplied to the user with the cuneiform cut guide removably attached to the first ray alignment guide.

In yet another aspect, the cuneiform multi-tool preferably includes a means for enabling forced translation of the first ray alignment guide along its longitudinal length to cause translation of the metatarsal toward or away from the medial cuneiform. The corresponding clinical effect is compression of the TMT joint after joint preparation has been performed, or distraction of the TMT joint to enable joint preparation, respectively. In a preferred embodiment, compressor-distractor is configured as a first cam with an axle attached to a second cam which includes a lever, the first cam imparting the compression-distraction force and the second cam imparting both a torsional force on the first cam and a locking force between the first ray alignment guide and the metatarsal base scaffold. Preferably, the metatarsal base scaffold includes a hole at the distal end, respective to the metatarsal anatomy, for receiving the cam axle. The first ray alignment guide preferably includes buttress members separated by a distance along the longitudinal axis and at the distal end, respective to the metatarsal, of the first ray alignment guide. The force imparted against a first ray alignment guide buttress member by the first cam is directed along the longitudinal axis of the metatarsal base scaffold and is inversely reacted through the attachment of the compressor-distractor axle within the metatarsal base scaffold hole thereby causing translation between the first ray alignment guide and the metatarsal base scaffold along the longitudinal axis of the first ray alignment guide. The torsional force imparted by the second cam causes the first cam to rotate thereby engaging and moving the first ray alignment guide relative to the metatarsal base scaffold. Translation of the metatarsal base scaffold relative to the first ray alignment guide thereby imparts compression or distraction of the TMT joint.

In a further aspect, the preferred present invention is directed to a method of performing bunion correction and joint fusion with a metatarsal multi-tool, a first ray multi-tool, and a cuneiform cut guide, wherein the metatarsal multi-tool is secured to the dorsal surface of the first metatarsal and the base of the first metatarsal is cut. The metatarsal multi-tool is then replaced by the first ray multi-tool, the first metatarsal is repositioned to a corrected anatomical position, and the first ray multi-tool is secured to the cuneiform with bone pins, wherein two bone pins are secured through two parallel tapered holes on the upper surface of the proximal end of the first ray alignment guide and one bone pin at an oblique angle to the parallel bone pins. The cuneiform head is cut, and the user removes the oblique bone pin and rotates the first metatarsal and attached first ray multi-tool without removing the parallel bone pins. After the first metatarsal rotation, the oblique bone pin is inserted to secure the first ray multi-tool and associated first ray of the foot. The user then rotates the second cam lever of the compressor-distractor imparting a torsional force against the first cam thereby translating the metatarsal base scaffold toward the medial cuneiform. The translation of the metatarsal causes compression of the TMT joint and the user rotates the second cam lever repositioning the second cam lever such that it is generally directed along the axis of the cam axle thereby locking the cam to maintain the compressive force of the metatarsal against the cuneiform. In relatively simple terms, the procedure involves distracting the joint and activating, preferably by pivoting or rotating, the compressor-distractor assembly and locking the compressor-distractor assembly, preferably by pivoting a cam lever handle ninety degrees relative to a generally horizontal cam lever center axis.

In a further aspect, the preferred present invention is directed to a method of distracting the TMT joint with a first ray multi-tool with the cuneiform cut guide removed. The first ray alignment guide is secured to the dorsal surface of the first metatarsal with bone pins, wherein two bone pins are placed through the parallel holes, and one is placed through the oblique hole. The first metatarsal is repositioned to a corrected anatomical position, and the first ray multi-tool is secured to the cuneiform with bone pins, wherein two bone pins are secured through two parallel tapered holes on the upper surface of the proximal end of the first ray alignment guide and one bone pin at an oblique angle to the parallel bone pins. The user then rotates the second cam lever of the compressor-distractor imparting a torsional force against the first cam thereby translating the metatarsal base scaffold away from the medial cuneiform. The translation of the metatarsal causes distraction of the TMT joint and the user rotates the second cam lever repositioning the second cam lever such that it is generally directed along the axis of the cam axle thereby locking the cam to maintain the distraction force holding open the TMT joint space.

In yet another aspect, an alternative means for enabling forced translation of the first ray alignment guide along its longitudinal length to cause translation of the metatarsal toward or away from the medial cuneiform includes compressor-distractor configured as a rack and pinion drive with a pinion axle attached to a cam which includes a lever, the pinion drive imparting the compression-distraction force, and the cam imparting both a torsional force on the pinion drive and a locking force between the first ray alignment guide and the metatarsal base scaffold. Preferably, the metatarsal base scaffold includes a hole at the distal end, respective to the metatarsal anatomy, for receiving the pinion axle. The first ray alignment guide preferably includes a slot along the longitudinal axis and at the distal end, respective to the metatarsal, of the first ray alignment guide and includes a rack along one side of the slot. The force imparted against a first ray alignment guide rack by the pinion drive is directed along the longitudinal axis of the metatarsal base scaffold and is inversely reacted to through the attachment of the pinion axle within the metatarsal base scaffold hole thereby causing translation between the first ray alignment guide and the metatarsal base scaffold along the longitudinal axis of the first ray alignment guide. The torsional force imparted by the cam lever causes the pinion drive to rotate about the pinion axle thereby engaging and moving the first ray alignment guide relative to the metatarsal base scaffold. Translation of the metatarsal base scaffold relative to the first ray alignment guide thereby imparts compression or distraction of the TMT joint.

In a further aspect, the preferred present invention is directed to a method of performing bunion correction and joint fusion with a metatarsal multi-tool, a first ray multi-tool, and a cuneiform cut guide, wherein the metatarsal multi-tool is secured to the dorsal surface of the first metatarsal and the base of the first metatarsal is cut. The metatarsal multi-tool is then replaced by the first ray multi-tool, the first metatarsal is repositioned to a corrected anatomical position, and the first ray multi-tool is secured to the cuneiform with bone pins, wherein two bone pins are secured through two parallel tapered holes on the upper surface of the proximal end of the first ray alignment guide and one bone pin at an oblique angle to the parallel bone pins. The cuneiform head is cut, the cuneiform cut guide is removed, and the user rotates the cam lever of the compressor-distractor about the pinion axle imparting a torsional force on the pinion drive thereby translating the metatarsal base scaffold toward the medial cuneiform. The translation of the metatarsal causes compression of the TMT joint and the user then rotates the cam lever about an axis perpendicular to the pinion axle axis repositioning the cam lever such that it is generally directed along the axis of the pinion axle thereby locking the cam to maintain the compressive force of the metatarsal against the cuneiform.

In a further aspect, the preferred present invention is directed to a method of distracting the TMT joint with a first ray multi-tool with the cuneiform cut guide removed. The first ray alignment guide is secured to the dorsal surface of the first metatarsal with bone pins, wherein two bone pins are placed through the parallel holes, and one is placed through the oblique hole. The first metatarsal is repositioned to a corrected anatomical position, and the first ray multi-tool is secured to the cuneiform with bone pins, wherein two bone pins are secured through two parallel tapered holes on the upper surface of the proximal end of the first ray alignment guide and one bone pin at an oblique angle to the parallel bone pins. The user then rotates the cam lever about the pinion axle of the compressor-distractor imparting a torsional force on the pinion drive thereby translating the metatarsal base scaffold away from the medial cuneiform. The translation of the metatarsal causes distraction of the TMT joint and the user rotates the cam lever about an axis perpendicular to the pinion axle axis repositioning the cam lever such that it is generally directed along the axis of the pinion axle thereby locking the cam to maintain the distraction force holding open the TMT joint space.

In yet another aspect, a means for cutting two different amounts of the base of a metatarsal or the head of a cuneiform includes a cut guide insert symmetric about a transverse axis and having a single slot proximal to a longitudinal axis. The cut guide insert is configured to be removably inserted into the aperture of a second embodiment of the metatarsal multi-tool, whereby the longitudinal dimension of the cut guide is aligned with the longitudinal dimension of the aperture of the metatarsal multi-tool with the cut guide slot either proximally oriented within the aperture or distally oriented within the aperture relative to the anatomy. In the case of a metatarsal base cut, when the cut guide insert is inserted into the aperture of the metatarsal multi-tool such that the slot is proximally oriented within the aperture, the slot is closer to the metatarsal base relative to when the cut guide insert is inserted into the aperture of the metatarsal multi-tool such that the slot is distally oriented within the aperture. It is contemplated that the cut guide insert may be implemented in a similar manner for removable insertion into the first ray alignment guide for cutting the cuneiform head.

In a further aspect, the preferred present invention is directed to a method of performing a base cut of a metatarsal with a metatarsal multi-tool or cut guide and a cut guide insert, wherein the metatarsal multi-tool is secured to the dorsal surface of the first metatarsal and the cut guide insert is removably inserted into the aperture of the metatarsal multi-tool. The system and method are not limited to manipulating and performing the preferred method on the TMT joint and may be designed and configured to manipulate bones associated with nearly any joint in the patient's body, preferably relatively small bone joints, and/or for manipulating bone particles or parts. In a first preferred embodiment, the cut guide insert is inserted into the aperture of the metatarsal multi-tool such that the slot is proximally oriented within the aperture. A bone saw is inserted into the cut guide insert slot and a first cut of the metatarsal base is performed and may be removed. If the user subsequently determines that an additional amount of bone is to be removed from the proximal end of the metatarsal, the cut guide insert is then removed from the metatarsal multi-tool and re-inserted into the aperture of the metatarsal multi-tool such that the slot is distally oriented within the aperture. A bone saw is inserted into the cut guide insert slot and a second cut of the metatarsal is performed at a location more distal to the first cut, thereby enabling removal of a portion of the proximal end of the metatarsal larger than that provided by the first bone cut. The bone portion of the second cut may then be removed. A first cut may be performed with the cut guide insert inserted into the aperture of the metatarsal multi-tool such that the slot is distally oriented within the aperture thereby enabling removal of a larger portion of the proximal end of the metatarsal without performing a second cut. It is further contemplated in a further aspect of the preferred present invention that a method of performing a head cut of a medial cuneiform may be performed in a similar manner to that described for a metatarsal base cut whereby a cut guide insert is removably inserted into a first ray multi-tool aperture or a cuneiform cut guide aperture. It should be further understood that any combination of cut guide insert orientations for removing both metatarsal base and a medial cuneiform head portions of bone will result in varying total amounts of bone removed from the TMT joint space.

In yet another aspect, the preferred present invention includes a means for rotating a metatarsal about its longitudinal axis. In a preferred embodiment the first ray multi-tool includes a first ray alignment guide having a curved body portion configured to receive a rotation insert, the rotation insert having a correspondingly curved surface such that the rotation insert is capable of rotating within first ray alignment guide perpendicular to its longitudinal axis. The rotation insert is configured to contain the metatarsal base scaffold such that the metatarsal base scaffold is secured from rotating relative to the rotation insert longitudinal axis and can translate along its longitudinal axis. In operation, the cuneiform portion of the first ray alignment guide is fixed to the medial cuneiform with bone pins and the metatarsal base scaffold is fixed to the first metatarsal with bone pins. The metatarsal base scaffold is capable of both rotation generally about the longitudinal axis of the first metatarsal and translation generally along the longitudinal axis of the first metatarsal relative to the first ray alignment guide and thereby the medial cuneiform.

In yet another aspect, the first ray multi-tool preferably includes a means for enabling forced translation of the metatarsal base scaffold along its longitudinal length to cause translation of the metatarsal toward or away from the medial cuneiform. The corresponding clinical effect is compression of the TMT joint after joint preparation has been performed, or distraction of the TMT joint to enable joint preparation, respectively. In a preferred embodiment, compressor-distractor is configured as a first cam with an axle attached to a second cam which includes a lever, the first cam imparting the compression-distraction force and the second cam imparting both a torsional force on the first cam and a locking force between the first ray alignment guide and the metatarsal base scaffold. Preferably, the first ray alignment guide includes a slot or hole at the distal end, respective to the metatarsal anatomy, for receiving the cam axle. The metatarsal base scaffold includes at least one hole generally perpendicular to its longitudinal axis and a bone pin capable of being inserted through the hole and into the first metatarsal. The first cam preferably is configured as a slot cam whereby the slot is configured to receive the bone pin. The force imparted against the bone pin by the cam slot is directed along the longitudinal axis of the metatarsal base scaffold and is inversely reacted to through the attachment of the compressor-distractor axle fixed within the first ray alignment guide hole or slot thereby causing translation between the first ray alignment guide and the metatarsal base scaffold along the longitudinal axis of the first ray alignment guide. The torsional force imparted by the second cam causes the first cam to rotate thereby engaging and moving the metatarsal base scaffold relative to the first ray alignment guide. Translation of the metatarsal base scaffold relative to the first ray alignment guide thereby imparts compression or distraction of the TMT joint.

In a further aspect, the preferred present invention is directed to a method of rotating a first metatarsal and compressing or distracting the first metatarsal against or away from a medial cuneiform comprising a tarsometatarsal joint. After preparation of the tarsometatarsal joint for fusion, in a first preferred embodiment the first ray multitool is secured to the first metatarsal with parallel bone pins placed through holes in the metatarsal base scaffold component in a generally dorsal-plantar orientation. The first ray multi-tool includes a slot cam compressor-distractor mechanism, having one bone pin positioned within the cam slot, and a metatarsal base scaffold capable of rotation generally about the first metatarsal longitudinal axis and translation generally along the first metatarsal longitudinal axis. The first metatarsal is aligned to a desired intermetatarsal angle, and the cuneiform portion of the first ray alignment guide component is secured to the medial cuneiform with bone pins. The metatarsal is rotated generally about its longitudinal axis until a desired rotational orientation is reached. The slot cam is then rotated to either compress or distract the TMT joint and the locking mechanism of the compressor-distractor component is activated to fix the position of the first metatarsal relative to the medial cuneiform. The first metatarsal and medial cuneiform are then secured with standard bone fixation devices.

Briefly stated, in preferred embodiments, a kit for adjusting a first metatarsal of a patient relative to a medial cuneiform includes a base scaffold, a first ray alignment guide, a first bone pin and a second bone pin. The base scaffold has a scaffold axis, a top surface, a first scaffold hole extending through the base scaffold and the top surface, and a guide surface. The first ray alignment guide is movably mountable to the base scaffold. The first ray alignment guide includes an alignment axis, a metatarsal side, a cuneiform side, and a cut aperture between the metatarsal side and the cuneiform side. The cuneiform side includes a first cuneiform hole extending therethrough. The metatarsal side includes a first metatarsal aperture extending therethrough and a first rail. The metatarsal side is preferably integrally formed with the cuneiform side. The first ray alignment guide is movably mountable to the base scaffold with the guide surface and the first rail guiding movement of the first ray alignment guide relative to the base scaffold generally parallel relative to the scaffold axis in a mounted configuration. The first rail may be comprised of nearly any feature that cooperates with the guide surface of the base scaffold to guide generally linear or translational movement of the first ray alignment guide relative to the base scaffold, generally parallel to the scaffold axis. The first scaffold hole is aligned with the first metatarsal aperture in the mounted configuration. The first bone pin is configured for connection to the first metatarsal and extension through the first scaffold hole and the first metatarsal aperture in the mounted configuration. The second bone pin is configured for connection to the medial cuneiform and extension through the first cuneiform hole. The base scaffold and first ray alignment guide facilitate alignment of the first metatarsal and the medial cuneiform and compression or distraction of the first metatarsal relative to the medial cuneiform in the mounted configuration.

In an additional aspect, a kit for adjusting a first metatarsal having a first metatarsal axis relative to a medial cuneiform includes a base scaffold, a cut guide, a first ray alignment guide, a compressor-distractor assembly and a first fastener. The base scaffold has a scaffold axis, a top surface, and a first scaffold hole extending through the base scaffold and the top surface. The cut guide includes a body, a cut guide slot, a cut guide axis and a positioner. The cut guide is configured for removable mounting to the first metatarsal such that the cut guide axis is oriented generally parallel to the first metatarsal axis. The cut guide slot and the positioner are oriented generally perpendicular to the cut guide axis. The first ray alignment guide has an alignment axis, a metatarsal side, a cuneiform side, a cut aperture between the metatarsal side and the cuneiform side, a first metatarsal aperture and a first cuneiform hole. The first ray alignment guide is configured for removable mounting to the first metatarsal and the medial cuneiform. The compressor-distractor assembly includes a compressor-distractor cam having a cam slot, a cam axle movably mounted in the cam slot and a cam lever. The cam axle extends through the first metatarsal aperture. The first fastener is configured to extend through the first scaffold hole to secure the base scaffold to the first metatarsal. The scaffold axis is oriented generally parallel to the first metatarsal when the base scaffold is secured to the first metatarsal.

In another aspect, the preferred invention is directed to a method for correcting a deformity between a first metatarsal, and a medial cuneiform using a kit having a base scaffold defining a scaffold axis, a cut guide with a cut guide slot, a first ray alignment guide, an alignment outrigger, a first fastener and a second fastener. The method includes mounting the base scaffold and the cut guide to the first metatarsal such that the scaffold axis is oriented generally parallel to the first metatarsal, the base scaffold mounted to the first metatarsal with the first fastener, cutting a first metatarsal base of the first metatarsal utilizing the cut guide slot, mounting the first ray alignment guide to the first metatarsal with the first fastener, orienting the alignment outrigger with the second metatarsal such that the alignment outrigger is positioned generally parallel to the second metatarsal, the alignment outrigger oriented substantially parallel to the scaffold axis, and securing the first ray alignment guide to the first metatarsal with the first fastener and to the medial cuneiform with the second fastener. The method may also include the steps of cutting a head of the medial cuneiform after positioning the alignment outrigger generally parallel to a second metatarsal to define a cuneiform cut plane, wherein cutting the first metatarsal base defines a metatarsal cut plane, the cuneiform cut plane being generally parallel relative to the metatarsal cut plane, and urging the first metatarsal toward the medial cuneiform after securing the first ray alignment guide to the medial cuneiform with the second fastener. The first fastener may be comprised of a first metatarsal bone pin and a second metatarsal bone pin, and the second fastener may be comprised of a first cuneiform bone pin and a second cuneiform bone pin. The alignment outrigger may be connected to a cuneiform cut guide, wherein the cuneiform cut guide has a positioning guide that interacts with a cut aperture of the first ray alignment guide to secure the cuneiform cut guide to the first ray alignment guide. The first ray alignment guide may be translatably mounted to the base scaffold such that the first ray alignment guide is translatable relative to the base scaffold generally parallel to the scaffold axis. A compressor-distractor assembly may be mounted to the first ray alignment guide, wherein the compressor-distractor assembly selectively secures the first ray alignment guide to the base scaffold or releases the first ray alignment guide from the base scaffold such that the first ray alignment guide may translate relative to the base scaffold generally along the scaffold axis. The first metatarsal may be pivoted about a first metatarsal axis of the first metatarsal and a distal end of the first metatarsal may be pivoted toward the second metatarsal when the alignment outrigger is aligned substantially parallel to the second metatarsal. The method may also include the step of distracting the first metatarsal away from the medial cuneiform after securing the base scaffold to the medical cuneiform with the second fastener. The base scaffold may be integrally formed with the cut guide, wherein the cut guide includes a positioner that is inserted into a tarsometatarsal joint before the first metatarsal base is cut. The base scaffold and the cut guide may be removed from the first metatarsal after cutting the first metatarsal base. The base scaffold may be comprised of a first base scaffold and a second base scaffold, wherein the first base scaffold is removably mounted to the cut guide and the second base scaffold is removably mounted to the first ray alignment guide. The cut guide may include a positioner extending generally parallel to the cut guide slot and positioned proximate the cut guide slot, wherein the positioner is configured for placement in a joint between the first metatarsal and the medial cuneiform to assist with orientation and cutting of the first metatarsal base.

BRIEF DESCRIPTION OF THE SEVERAL VIEWS OF THE DRAWINGS

The foregoing summary, as well as the following detailed description of preferred embodiments of the instruments or tools and methods of the present application, will be better understood when read in conjunction with the appended drawings. For the purposes of illustrating the tarsometatarsal joint arthrodesis tools, there are shown in the drawings preferred embodiments. It should be understood, however, that the application is not limited to the precise arrangements and instrumentalities shown. In the drawings:

FIG. 12a is an isometric view of the first ray multi-tool with the cuneiform cut guide removed attached to the medial cuneiform with parallel bone pins protruding through the lateral-most portion of the cuneiform holes after initial alignment correction of the first metatarsal;

FIG. 12b is an isometric view of the first ray multi-tool of FIG. 12a attached to the first metatarsal and medial cuneiform after additional frontal plane rotation of the first metatarsal with parallel bone pins now protruding through the medial-most portion of the cuneiform holes after correction of the first metatarsal;

FIG. 13 is an isometric view of the first ray multi-tool of FIG. 10 in a neutral compression-distraction position;

FIG. 20a is an isometric exploded side view of a pinion that may be utilized with the first ray alignment guide of FIG. 19 of the compressor-distractor mechanism;

FIG. 20b is a side elevational view of the pinion of FIG. 20a;

FIG. 21 is an isometric perspective view of the first ray alignment guide of FIG. 19 assembled with the pinion of FIG. 20a;

FIG. 22b is a top view of the cut guide insert of FIG. 22a;

FIG. 24a is a top plan view of the cut guide insert of FIG. 22a positioned within an aperture of the metatarsal multi-tool of FIG. 1;

FIG. 24b is a partial cross-sectional, side elevational view of the cut guide insert of FIG. 22a positioned within the aperture of the metatarsal multi-tool of FIG. 1 such that a slot is proximally oriented within the aperture;

FIG. 24c is a partial cross-sectional, side elevational view of the cut guide insert of FIG. 22a positioned within the aperture of the metatarsal multi-tool of FIG. 1 such that the slot is distally oriented within the aperture;

DETAILED DESCRIPTION OF THE INVENTION

Figure 1:
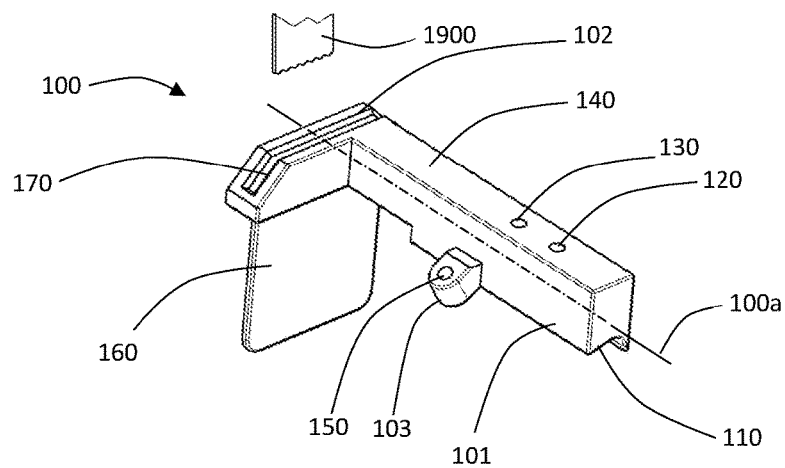
FIG. 1 is an isometric perspective view of a tarsometatarsal joint arthrodesis tool or metatarsal multi-tool or instrument, specifically a cut guide, in accordance with a first preferred embodiment of the present invention.

Certain terminology is used in the following description for convenience only and is not limiting. Unless specifically set forth herein, the terms "a", "an" and "the" are not limited to one element but instead should be read as meaning "at least one." The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred tools or instruments and related parts thereof. The words, "anterior", "posterior", "superior," "inferior", "lateral," "dorsal," and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component, insertion tool or related feature of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1-24c, the present disclosure describes a kit, an apparatus and a method for preferred embodiments of a set of tarsometatarsal joint arthrodesis tools or a kit for adjusting a first metatarsal 600 of a patient relative to a medial cuneiform 1140 and/or a second metatarsal 1100. The kit is described herein as facilitating adjustment of the first metatarsal 600 relative to the medial cuneiform 1140 and a second metatarsal 1100 but is not so limited. The kit, tools and instruments described herein may be utilized to manipulate, adjust, compress, cut, shave and/or distract bones or portions of bones relative to each other and/or to fix the bones or portions of bones relative to each other. The kit is preferably comprised of two or more instruments, tools, components or assemblies described herein for manipulating bones or bone segments that are provided to a user for conducting the desired procedure. The preferred kit is configured for adjusting a first metatarsal 600 of a patient relative to a medial cuneiform 1140.

Referring to FIGS. 1-10 a tarsometatarsal joint arthrodesis tool set or kit in accordance with preferred embodiments may comprise a metatarsal multi-tool or first preferred metatarsal cut guide 100 for securing to the first metatarsal 600 and preparing or cutting the articular surface of a first metatarsal base 600b of the first metatarsal 600. The cut guide 100 is preferably secured to the first metatarsal 600 such that a first cut guide axis 100a is oriented generally parallel to a first metatarsal axis 600a in a mounted configuration. The first preferred cut guide 100 includes a base scaffold 101 with a scaffold axis 100a, a bone contacting side 110, a top surface 140, first and second holes 120, 130 that extend through the top surface 140 and the bone contacting side 110, and a cut guide portion 102 having a positioner 160 that is oriented generally perpendicular relative to the first cut guide axis 100a and a multi-tool slot 170 that is oriented generally parallel relative to the positioner 160. In the first preferred embodiment, the base scaffold 101 and the cut guide 102 are integrally formed but this configuration is not so limiting and the base scaffold 101 and the cut guide 102 may be separately formed and assembled, as is described in greater detail herein with respect to additional preferred embodiments. The multi-tool slot 170 and the positioner are also oriented generally perpendicular to the first metatarsal axis 600a of the first metatarsal 600 in the mounted configuration.

The kit may also include a first ray alignment multi-tool assembly 1000 in accordance with a second preferred embodiment and a third preferred embodiment for removably attaching a cut guide 800, preferably a cuneiform cut guide 800, to the first metatarsal 600 and the medial cuneiform 1140 and aligning and securing the first metatarsal 600 in a corrected orientation. The cuneiform cut guide 800 may be configured for aiding alignment of the first metatarsal 600 to the second metatarsal 1100 and guiding a cutting blade 1900, preferably attached to a bone saw (not shown), for removal of a portion of a head articular surface or portion 1140a of the medial cuneiform 1140, and a compressor-distractor assembly 900 for imparting a force along the first metatarsal axis 600a of the first metatarsal 600 for translation of the first metatarsal 600 toward (compression) or away from (distraction) the tarsometatarsal joint space or the medial cuneiform 1140 and to lock the metatarsal multi-tool in a compressed or distracted position such that the realigned and compressed or distracted medical cuneiform 1140 and the first metatarsal 600 may be fixed by orthopedic hardware (not shown) relative to each other to correct a deformity between the medial cuneiform 1140 and the first metatarsal 600, the first metatarsal 600 relative to a second metatarsal 1100, or general deformity or misalignment of a first bone or bone portion relative to a second one or bone portion. The third preferred cuneiform cut guide 800 is preferably configured for removable mounting to the first ray alignment guide 700 at the cut aperture 740. The cut guide 800 includes a body 802, a cut guide slot 840 and an alignment outrigger 820. The alignment outrigger 820 includes an alignment leg 822 and the cut guide slot 840 is oriented substantially perpendicular to the alignment leg 822. The preferred cuneiform cut guide 800 includes a positioning guide 810 extending from the body 802 and the first ray alignment guide 700 includes supports 750 in the cut aperture 740. The positioning guide 810 interacts with the supports 750 to connect the cut guide 800 to the first ray alignment guide 700 when the cut guide 800 is mounted to the first ray alignment guide 700. The cuneiform cut guide 800 preferably includes a positioner 830 proximate and generally parallel to the cut guide slot 840 and is configured for placement into a joint between the first metatarsal 600 and the medial cuneiform 1140. The positioner 830 is configured to aid in orienting the cut guide slot 840 for cutting the medial cuneiform head 1140a of the medial cuneiform 1140.

Figure 28A:
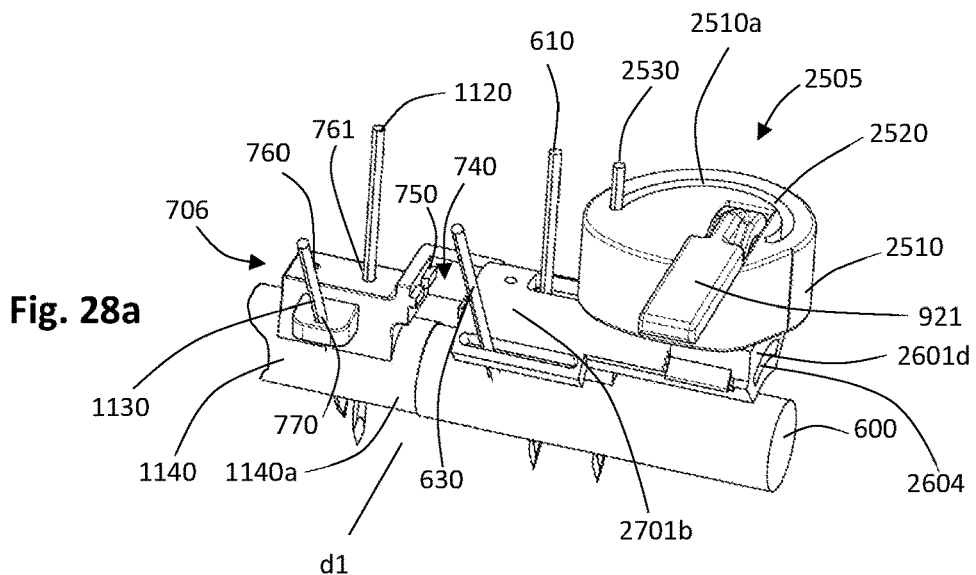
FIG. 28a is an isometric perspective view of the first ray multi-tool of FIG. 25 mounted to a bone in a compressed configuration.
Figure 28B:
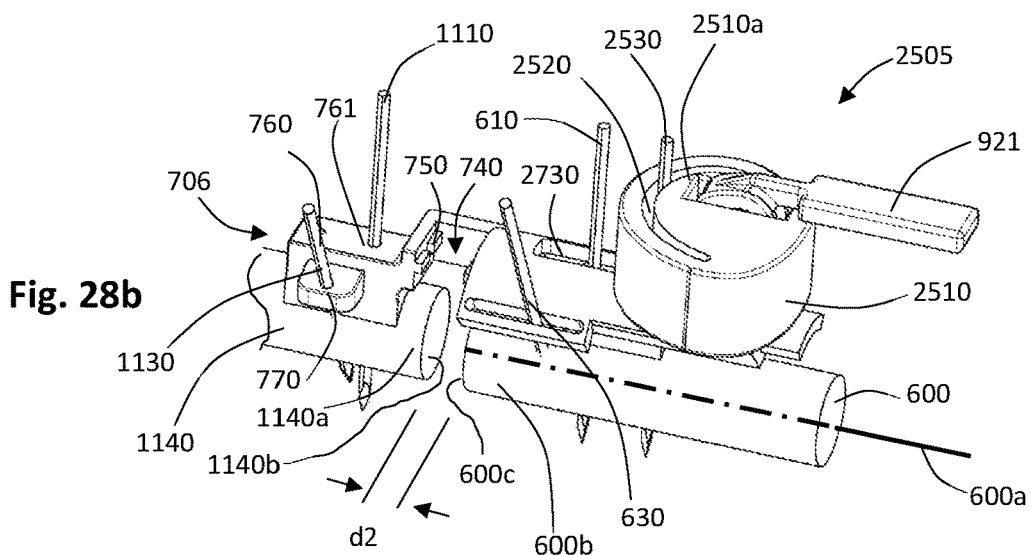
FIG. 28b is an isometric perspective view of the first ray multi-tool of FIG. 25 mounted to a bone in a partially distracted configuration.
Figure 28C:
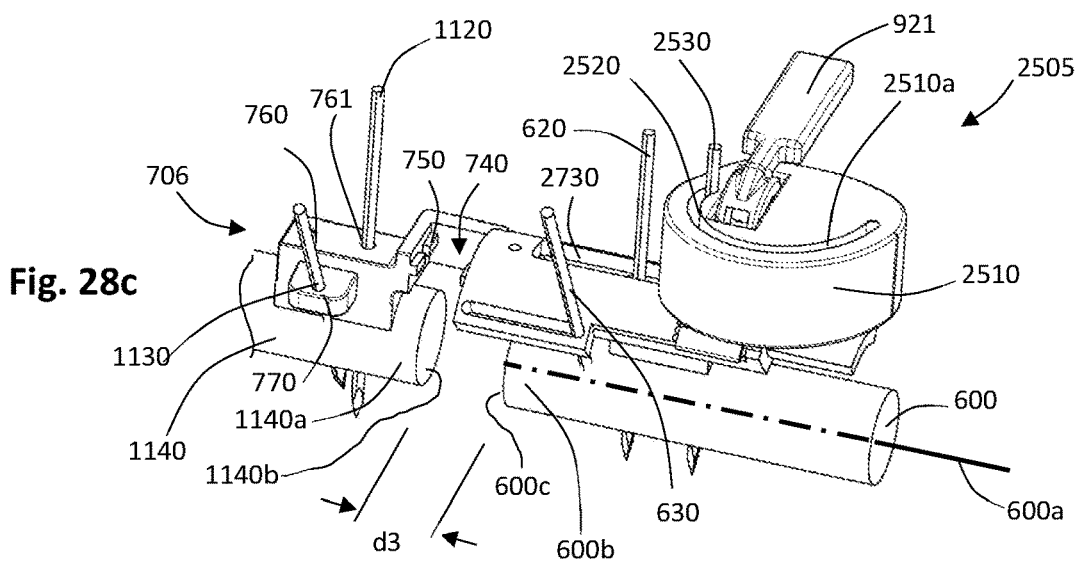
FIG. 28c is an isometric perspective view of the first ray multi-tool of FIG. 25 mounted to a bone in a distracted configuration.
Figure 29:
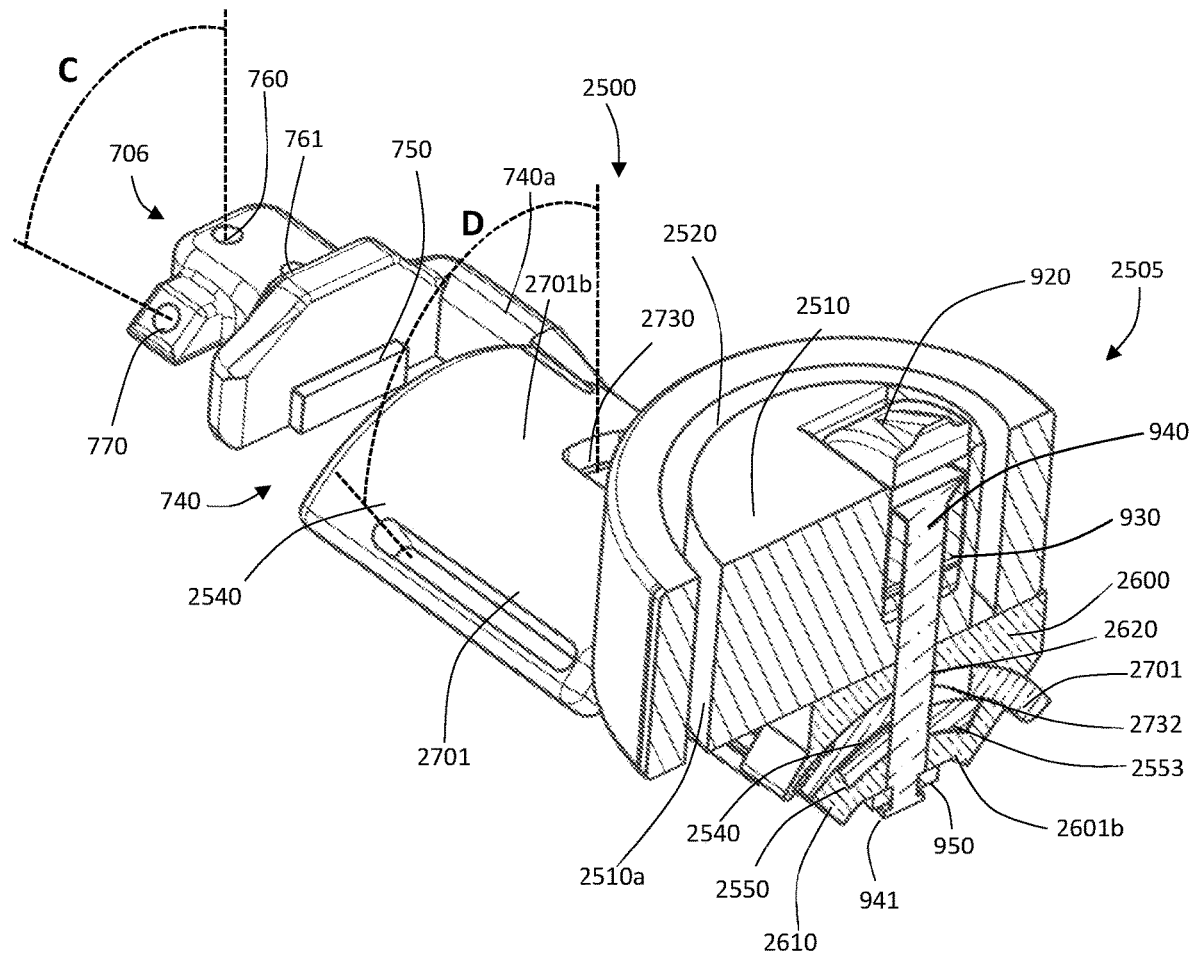
FIG. 29 is an isometric perspective cross-sectional view of the first ray multi-tool of FIG. 25, taken along line 29-29 of FIG. 25.
Figure 30:
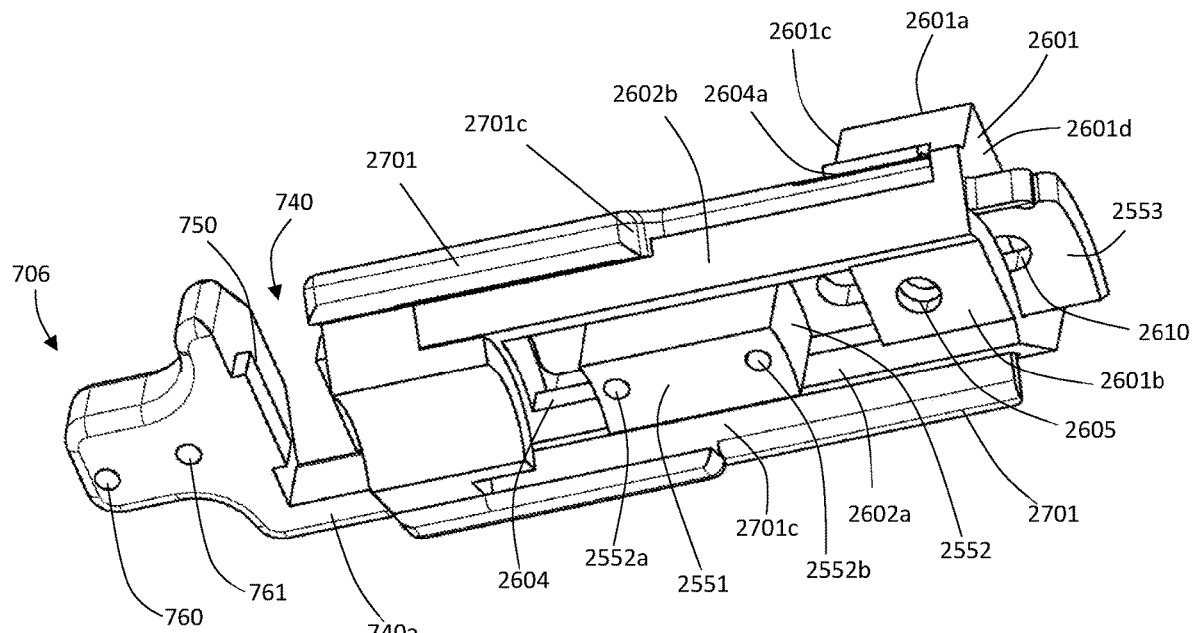
FIG. 30 is a bottom isometric perspective view of an assembled first ray alignment guide, base scaffold and rotation insert of the first ray multi-tool of FIG. 25.
Figure 31:
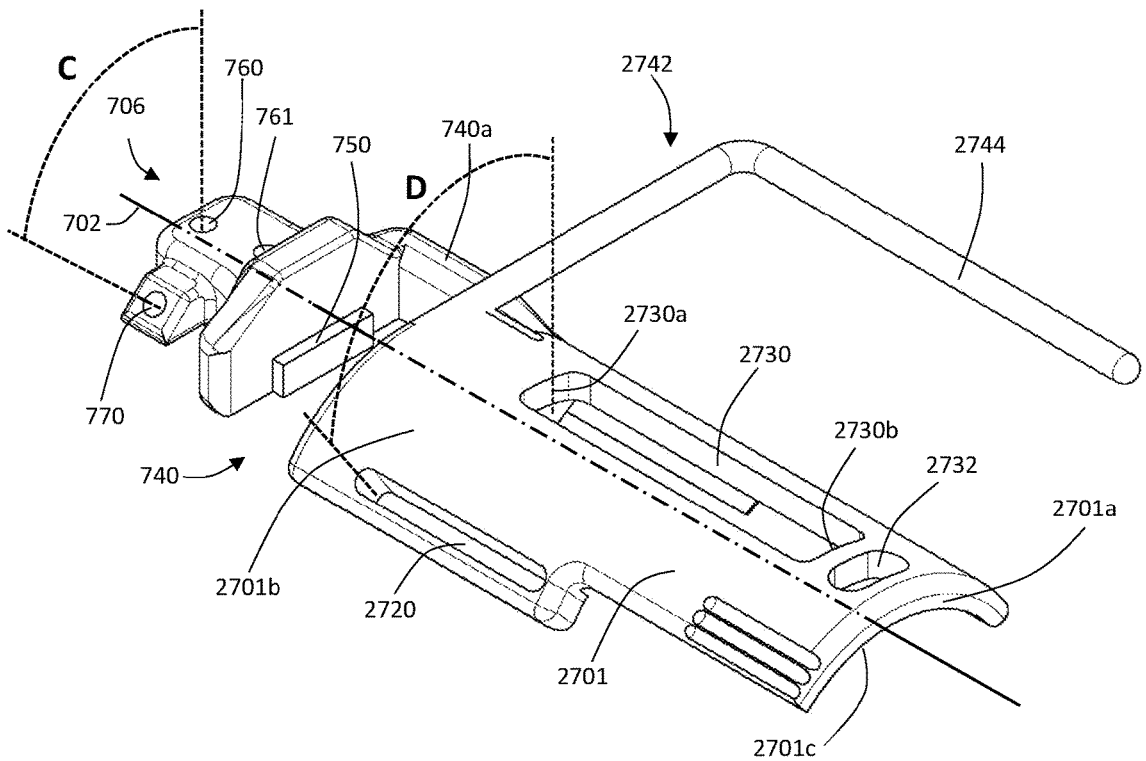
FIG. 31 is a top isometric perspective view of an alternative sixth preferred first ray alignment guide that may be utilized with the first ray multi-tool of FIG. 25, wherein the alternative sixth preferred first ray alignment guide would replace the first ray alignment guide of the sixth preferred embodiment in the first ray multi-tool.

Referring specifically to FIGS. 1-7, the first preferred embodiment of the metatarsal multi-tool or kit may include the cut guide 100, which is shown in isolation. A geometry of the bone-contacting side 110 of the base scaffold 101 is preferably configured to generally mirror typical anatomy of a dorsal surface of the first metatarsal 600 of a patient proximate to a first metatarsal base 600b. The first and second holes 120, 130 are included in the top surface 140 and extend through the base scaffold 101 of the metatarsal multi-tool or cut guide 100 through the bone-contacting side 110 and are preferably oriented parallel to each other and perpendicular to the top surface 140. The first and second holes 120, 130 are not limited to being oriented generally perpendicular to the top surface 140 and may be oriented at an angle relative to the top surface 140 or may being oriented such that the first hole 120 is generally perpendicular to the top surface 140 and the second hole 130 is oriented at angle relative to the top surface 140, which may improve stability of connection of the first cut guide 100 to the first metatarsal 600. The first hole 120 is configured to accept a first fastener, such as a first metatarsal bone pin 610, to secure the cut guide 100 to the first metatarsal 600. The first and second holes 120, 130 are preferably configured to accept the first bone pin 610 and a second bone pin 620, which together comprise the first fastener, for securing the metatarsal multi-tool or cut guide 100 to the first metatarsal 600. An angled metatarsal hole 150, which is positioned in an angled boss 103 extending from a side of the base scaffold 102, of the metatarsal multi-tool or cut guide 100 is configured to accept a third metatarsal bone pin 630 with an axis oblique to the axes of first and second holes 120, 130 such that the first and second metatarsal bone pins 610, 620 are generally oriented parallel relative to each other in the mounted configuration and the third metatarsal bone pin 630 is preferably oriented at an angle relative to the first and second metatarsal bone pins 610, 620 in the mounted configuration. The orientations of the first and second holes 120, 130 and the angled metatarsal hole 150 are preferably configured to direct the first, second, and third metatarsal bone pins 610, 620, 630 toward the first metatarsal axis 600a in a working configuration. The positioner 160 has a geometry configured to generally fit within the tarsometatarsal joint space between the first metatarsal 600 and the medial cuneiform 1140 and abut the first metatarsal base 600b of the first metatarsal 600 in a mounted configuration. The multi-tool slot 170 is configured with a surface proximate and parallel to the positioner 160 and a geometry configured to accept a bone saw with the cutting blade 1900 for cutting an articular surface of the first metatarsal base 600b to define a metatarsal cut plane 600c (FIGS. 28b and 28c) following the cut that is generally planar and is preferably oriented generally perpendicular to the first metatarsal axis 600a and the first cut guide axis 100a or the scaffold axis 202, depending on whether the first preferred cut guide 100 or the assembled base scaffold 200 and a second preferred metatarsal cut guide 300 is mounted to the first metatarsal 600. The metatarsal cut plane 600c is preferably oriented generally perpendicular to the first metatarsal axis 600a and parallel to the positioner 160 and the multi-tool slot 170 when the cut guide 100 is in the mounted configuration after the first metatarsal base 600b is cut.

A second preferred embodiment of a metatarsal multi-tool or kit may include a cut guide 300 and a base scaffold 200. The multi-tool of the second preferred embodiment is preferably configured as an assembly comprised of the base scaffold 200 and the cut guide 300. The base scaffold 200 includes a scaffold axis 202, a top surface 240, and a bone-contacting side 210 that is preferably configured to generally mirror typical anatomy of the dorsal surface of the first metatarsal 600 proximate to the first metatarsal base 600b. First and second scaffold holes 220, 230 are included in the metatarsal base scaffold 200 that extend through a top surface 240 and the bone-contacting side 210 and are oriented parallel to each other and perpendicular to the top surface 240 of the base scaffold 200. The first and second scaffold holes 220, 230 are configured to accept a first fastener, preferably the first and second bone pins 610, 620, for securing the base scaffold 200 to the first metatarsal 600 in the mounted configuration. An angled hole 250 of the base scaffold 200 is configured to accept a third metatarsal bone pin 630 that defines an arcuate angle relative to the axes of the first and second scaffold holes 220, 230 in the mounted configuration. The angled hole 250 is preferably formed in an angled boss 251 extending from a first side 281 of the base scaffold 200. An axle hole 260 is positioned proximate a second side 290 of the base scaffold 200 and is configured to receive a cam axle 940 of a compressor-distractor assembly 900, as is described in greater detail below. A threaded hole 270 is positioned proximate a near side 204 of the base scaffold 200 and is configured to receive an attachment knob 400 for securing other tools to the top surface 240, such as the metatarsal cut guide 300 of the second preferred embodiment. The base scaffold 200 also includes a guide surface 280, 290, 281, 291 that interacts with a first rail 710, 720, 711, 721 of a first ray alignment guide 700 to guide movement of the first ray alignment guide 700 relative to the base scaffold 200, generally parallel relative to a scaffold axis 202 of the base scaffold 200. The first ray alignment guide 700 is movably mounted to the base scaffold 200 and includes an alignment axis 702, a metatarsal side 704, a cuneiform side 706, and a cut aperture 740 between the metatarsal side 704 and the cuneiform side 706. The metatarsal side 704 and the cuneiform side 706 are preferably aligned along the alignment axis 702 and are connected across the aperture 740 by an aperture leg 740a. In the second preferred embodiment, the guide surface is comprised of first and second sides 280, 290 and first and second slots 281, 291 that extend generally parallel to the scaffold axis 202 wherein the first and second slots 281, 291 are configured to slidably receive the first rail 711, 721 and the first and second sides 280, 290 are configured to slidably interact with corresponding sides 710, 720 of a first ray alignment guide 700. The first and second slots 281, 291 extend from the near side 204 to a far side 206 of the base scaffold but are not so limited and may extend a limited length along the first and second sides 280, 290, depending on a configuration of the base scaffold 200 and the first ray alignment guide 700. The guide surface 280, 290, 281, 291 of the base scaffold 200 and the first rail 710, 720, 711, 721 of the first ray alignment guide 700 are not limited to being comprised of the sides 280, 290, 710, 720 and slots or rails 281, 291, 711, 721 of the second preferred embodiment and may be comprised of nearly any mechanism or feature that facilitates translational movement of the first ray alignment guide 700 relative to the base scaffold 200 when assembled.

The base scaffold 200 of the second preferred embodiment may be comprised of the same base scaffold 200 utilized with the cut guide 300 or may be a separate base scaffold 200 that is dedicated for use with the first ray alignment guide 700 and the compressor-distractor assembly 900, such as when the base scaffold 200 is comprised of first and second base scaffolds 200 that are provided in a kit to the user along with the metatarsal cut guide 300, the first ray alignment guide 700, and the compressor-distractor assembly 900. The first and second base scaffolds 200 may be pre-assembled with the metatarsal cut guide 300 and the first ray alignment guide 700 and the compressor-distractor assembly 900, respectively, in the kit. The kit is not limited to including the components in these pre-assembled configurations, but the components may be pre-assembled for ease of use and efficiency for the user. The kit may also include the cuneiform cut guide 800 for selective mounting to the cut aperture 740 but is similarly not limited.

Figure 6:
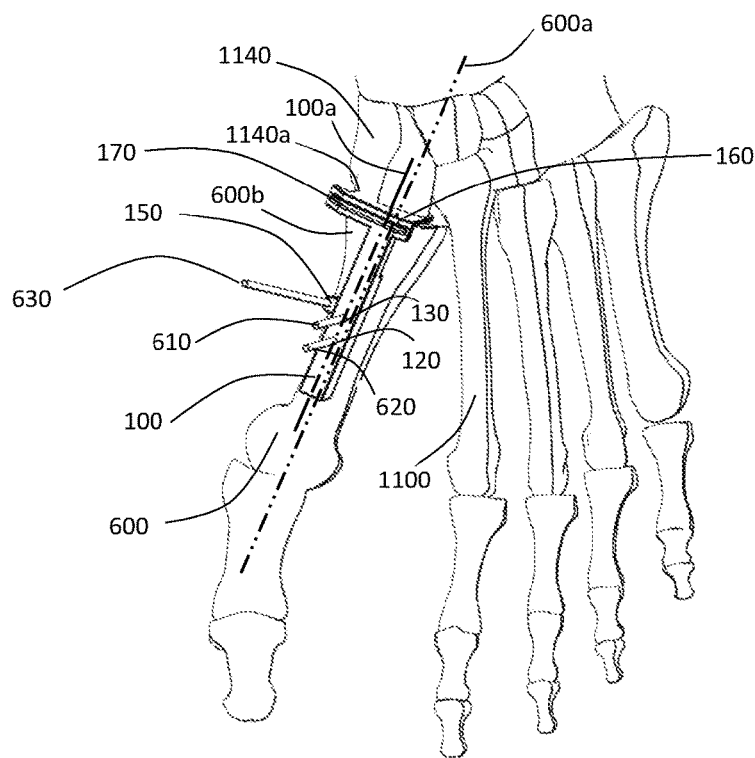
FIG. 6 is a dorsal view of the metatarsal multi-tool of FIG. 1 secured to a first metatarsal in an uncorrected alignment with the medial cuneiform.

The metatarsal cut guide 300 may be utilized with and is configured to be removably attachable to the base scaffold 200. A first cut guide hole or anchor hole 310 is formed in the metatarsal cut guide 300 that extends through top and bottom surfaces of the metatarsal cut guide 300. The anchor hole 310 is configured to allow insertion of a threaded attachment knob 400 through the anchor hole 310 and into the threaded hole 270 of the base scaffold 200 for securing the metatarsal cut guide 300 to the base scaffold 200. First and second cut guide holes 320, 330 of the metatarsal cut guide 300 are preferably oriented parallel to each other and perpendicular to the top surface 340 of the metatarsal cut guide 300. The first and second cut guide holes 320, 330 are preferably configured to align with the first and second scaffold holes 220, 230 of the base scaffold 200 when attached. A positioner 360 has a geometry configured to generally fit within a tarsometatarsal joint space between the first metatarsal 600 and the medial cuneiform 1140 and abut a first metatarsal base 600b of the first metatarsal 600 in a working configuration (FIG. 6). A multi-tool slot 370 is defined in the cut guide 300 and is oriented generally parallel to the positioner 360. The multi-tool slot 370 is configured to accept the cutting blade 1900 of the bone saw for cutting the articular surface of the first metatarsal base 600b of the first metatarsal 600. Following the cut, the first metatarsal cut plane 600c is preferably defined on the first metatarsal 600 that is oriented generally parallel to the multi-tool slot 370 and perpendicular to the first metatarsal axis 600a and the scaffold axis 202.

The threaded attachment knob 400 is configured to be removably attachable to the base scaffold 200 using the threaded hole 270 of the base scaffold to securely connect tools to the base scaffold 200. A threaded shaft 410 of the attachment knob 400 is configured with threads and a preferred length corresponding to the geometry of threaded hole 270. A head 420 of the attachment knob 400 is securely attached to the threaded shaft 410 and dimensioned appropriately for manipulation by the user. In the preferred embodiment, the knob 400 is utilized for attaching the metatarsal cut guide 300 or the first ray alignment guide 700 to the base scaffold 200, but these components are not so limited and may be otherwise connected by alternative fasteners, clamping, bonding or other connection mechanisms or techniques to secure the components together.

The metatarsal cut guide 300 of the second preferred embodiment is removably attachable to the base scaffold 200 for preparing the first metatarsal base 600b by cutting or shaving the articular surface of the first metatarsal base 600b to define the first metatarsal cut plane 600c. The threaded attachment knob 400 is preferably utilized with the anchor hole 310 of the metatarsal cut guide 300 and the threaded hole 270 of the base scaffold 200 to secure the base scaffold 200 to the metatarsal cut guide 300. This removable attachment of the base scaffold 200 and the metatarsal cut guide 300 in the working configuration has a similar operation and function when compared to the first preferred embodiment of the tarsometatarsal joint arthrodesis tool or metatarsal multi-tool cut guide 100.

In operation, the metatarsal multi-tool or first preferred metatarsal cut guide 100 is secured to the first metatarsal 600 that is mal-aligned relative to normal anatomy, which may correspond to a hallux valgus deformity otherwise referred to as a bunion or other mal-alignment of the first metatarsal 600 or another bone or bone portion. In the first preferred embodiment, the metatarsal multi-tool or metatarsal cut guide 100 is placed on the dorsal aspect of the first metatarsal 600 such that a first cut guide axis 100a is aligned with a first metatarsal axis 600a with the positioner 160 inserted within the tarsometatarsal joint space and abutting the first metatarsal base 600a of the first metatarsal 600. The first cut guide axis 100a of the first preferred metatarsal multi-tool or metatarsal cut guide 100 is oriented in general alignment with the first metatarsal axis 600a of the first metatarsal 600. First, second and third metatarsal bone pins 610, 620, 630 are inserted into the first and second holes 120, 130 of the metatarsal cut guide 100, and the angled metatarsal hole 150 to secure the metatarsal multi-tool or metatarsal cut guide 100 to the first metatarsal 600. The first, second and third metatarsal bone pins 610, 620, 630 preferably include the first metatarsal bone pin 610, the second metatarsal bone pin 620 and the third metatarsal bone pin 630. In the preferred embodiment, the cutting blade 1900 of the bone saw (not shown) is inserted into the metatarsal multi-tool slot 170 and the articular surface of the first metatarsal base 600b is removed, resulting in a generally planar surface at the first metatarsal cut plane 600c that is oriented substantially perpendicular to the first cut guide axis 100a.

Figure 7:
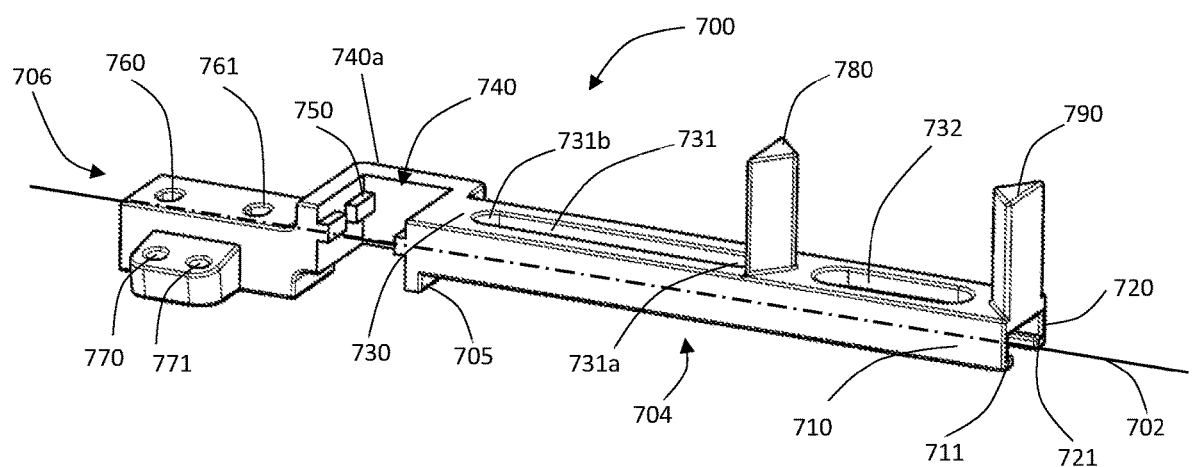
FIG. 7 is an isometric perspective view of a first ray alignment guide in accordance with a third preferred embodiment of the present invention configured for vertical removable attachment of a cuneiform cut guide and permanent attachment of a compressor-distractor.

Referring to FIG. 7, a first ray alignment guide 700 is configured to be slidably attached to the base scaffold 200, preferably such that the first ray alignment guide 700 is translatable relative to the base scaffold 200 generally parallel to the scaffold axis 202. The base scaffold 200 preferably includes the scaffold axis 202, the top surface 240, the first and second scaffold holes 220, 230 extending through the base scaffold 200 and the top surface 240 and a guide surface 280, 281, 290, 291. The first and second sides 710, 720 of the first ray alignment guide 700 are preferably perpendicular to a top surface 730 of the first ray alignment guide 700 and are configured to slidably abut first and second sides 280, 290 of the base scaffold 200 and first and second rails 711, 721 of the first ray alignment guide 700. The first and second rails 711, 721 are preferably configured to slidably insert into first and second slots 281, 291 of the metatarsal base scaffold 200 in a working configuration. The first ray alignment guide 700 is movably mountable to the base scaffold 200 with the guide surface 280, 281, 290, 291 and the first rail 710, 711, 720, 721 guiding movement of the first ray alignment guide 700 relative to the base scaffold 200 generally parallel relative to the scaffold axis 202 in a mounted configuration.

The first ray alignment guide 700 includes an alignment axis 702, a metatarsal side 704, a cuneiform side 706 and a cut aperture 740 between the metatarsal side 704 and the cuneiform side 706. The cuneiform side 706 includes a first cuneiform hole 760 extending therethrough, generally perpendicular to the alignment axis 702. The metatarsal side 704 includes a first metatarsal aperture 731 extending therethrough and the first rail 710, 711, 720, 721. The first metatarsal aperture 731 and the first rail 710, 711, 720, 721 are configured to allow the metatarsal base scaffold 200 with the first and second metatarsal bone pins 620, 630 positioned in the first and second scaffold holes 220, 230 and the first metatarsal 600 to translate relative to the first ray alignment guide 700 without impediment, at least until the first or second metatarsal bone pins 620, 630 contact first or second sides 731a, 731b of the first metatarsal aperture 731, respectively, or other stops of the base scaffold 200 and the first ray alignment guide 700 prevent further translation. The first scaffold hole 220 is aligned with the first metatarsal aperture 731 in the mounted configuration. The metatarsal side 704 and the cuneiform side 706 are integrally formed. In the third preferred embodiment, the first metatarsal aperture 731 is comprised of a slot that extends through the metatarsal side 704, is oriented generally parallel to the alignment axis 702 and is sized and configured to accommodate the first and second metatarsal bone pins 620, 630. In the third preferred embodiment, the first ray alignment guide 700 also includes a second metatarsal aperture 732 that is configured to cooperate with a third preferred compressor-distractor assembly 900 (FIG. 9), as will be described in greater detail below, and is specifically configured to facilitate extension of a cam axle 910 therethrough to selectively release and lock the position of the first ray alignment guide 700 relative to the base scaffold 200. The first ray alignment guide 700 is not limited to including the first and second metatarsal apertures 731, 732 and may include a single aperture or slot, additional apertures or slots, holes or other features that facilitate connection of the base scaffold 200 to the first metatarsal 600 and selective release and locking of the first ray alignment guide 700 relative to the base scaffold 200.

Figure 8A:
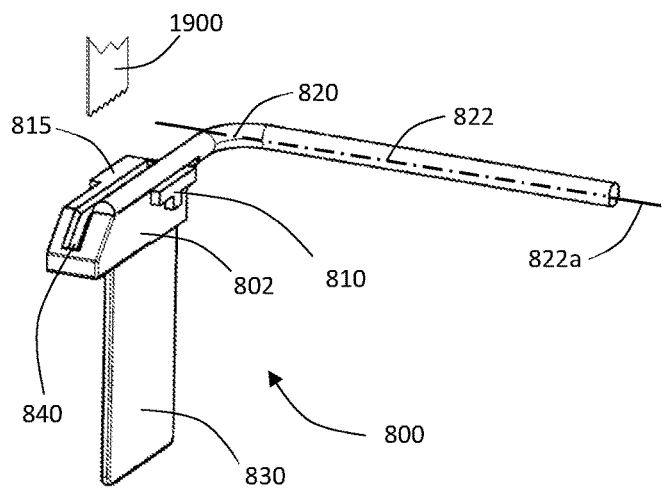
FIG. 8a is an isometric view of a cuneiform cut guide.
Figure 8B:
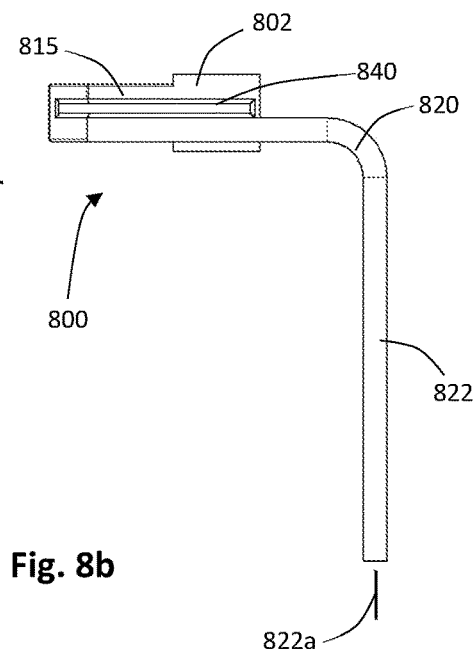
FIG. 8b is a dorsal view of a cuneiform cut guide.

Referring to FIGS. 7-8B, the cut aperture 740 of the first ray alignment guide 700 is configured to facilitate preparation or a cut of the head articular surface 1140a of the medial cuneiform 1140 to define a cuneiform cut plane 1140b (FIGS. 28b and 28c) and for removable attachment of a cuneiform cut guide 800. The cuneiform cut guide 800 is preferably connected to the cut aperture 740 by interaction between supports 750 positioned within the cut aperture 740 and positioning guides 810 of the cuneiform cut guide 800. The supports 750 are configured to receive the corresponding positioning guides 810 of the cuneiform cut guide 800 to orient the cuneiform cut guide 800 relative to the first ray alignment guide 700 and the first metatarsal 600. The first ray alignment guide 800 also includes first and second cuneiform holes 760, 761 that extend through the cuneiform side 706. The first and second cuneiform holes 760, 761 are preferably aligned along the alignment axis 702, extend through the cuneiform side 706 generally parallel to each other and are preferably oriented perpendicular to the top surface 730. The first and second cuneiform holes 760, 761 are configured to accept first and second bone pins 1110, 1120 for securing the first ray alignment guide 700 to the medial cuneiform. The first and second cuneiform holes 760, 761 are preferably oriented generally perpendicular to the top surface of the cuneiform side 706 but are not so limited and may be otherwise oriented and configured to secure the cuneiform side 706 to the medial cuneiform 1140. The first cuneiform hole 760 may, for example, be oriented at an angle relative to the top surface of the cuneiform side 706 with the second cuneiform hole 761 oriented generally perpendicular to the top surface, which may increase stability of the connection of the cuneiform side 706 with the first and second cuneiform bone pins 1110, 1120. The first and second bone pins 1110, 1120 are not limited to being comprised of bone pins and may be comprised of fasteners, wires or other securing mechanisms or methods to secure the cuneiform side 706 to the medial cuneiform 1140.

First and second angled or off-axis holes 770, 771 of the cuneiform side 706 are also configured to accept bone pins, such as the third cuneiform bone pin 1130, with an axis oblique to the axes of the first and second cuneiform holes 760, 761 or defining an acute angle between the first and second angled holes 770, 771 and the first and second cuneiform holes 760, 761. The first ray alignment guide 700 of the third preferred embodiment may be designed and configured without the first and second angled or off-axis holes 770, 771 without significantly impacting the operation and function of the first ray alignment guide 700. First and second posts 780, 790 of the first ray alignment guide 700 extend upwardly from the top surface 730. The first post 780 is positioned between the first and second metatarsal apertures 731, 732 and the second post 790 is positioned at a distal end of the first ray alignment guide 700. The first and second posts 780, 780 are configured to be slidably in contact with a cam surface 910a of a compressor-distractor cam 910 of the compressor-distractor assembly 900 and react forces to translate the metatarsal base scaffold 200 along the alignment axis 702 of the first ray alignment guide 700 in reaction to torsional force applied to the compressor-distractor cam 910. When the base scaffold 200 is attached to the first metatarsal 600 and the first ray alignment guide 700 is secured to the medial cuneiform 1140, the compressor-distractor cam 910 is pivoted in a first direction and is configured to apply a cam force to the first and/or second posts 780, 790 that results in motion of the first metatarsal 600 away from the tarsometatarsal ("TMT") joint causing joint distraction while the compressor-distractor cam 910 may be pivoted in a second opposite direction resulting in a cam force applied to the first and/or second posts 780, 790, which results in motion of the first metatarsal 600 toward the tarsometatarsal joint causing joint compression. The first and second posts 780, 790 are generally in contact with the cam surface 910a or at least one of the first and second posts 780, 790 is in contact with the cam surface 910a during operation. The shape of the cam surface 910a in combination with the positioning of the cam axle hole 911 and the cam axle 940 and interaction of the cam axle 940 with the second metatarsal aperture 732 and the axle hole 260 of the base scaffold 200 results in the translation of the first metatarsal 600 and the medical cuneiform 1140 during operation.

Referring to FIGS. 7-8b and 11a-11c, the cuneiform cut guide 800 may include a plurality of positioning guides 810 having a variety of configurations that is configured to align the cuneiform cut guide 800 within the cut aperture 740 of the first ray alignment guide 700. In the second preferred embodiment, the cuneiform cut guide 800 is removably attachable to the alignment guide 700 by insertion from above the alignment guide top surface 730. A releasable catch comprised of the supports 750 and the positioning guide 810 of the cuneiform cut guide 800 are designed to releasably secure the cuneiform cut guide 800 to the first ray alignment guide 700. In use, alignment and abutment of the positioning guide 810 onto the supports 750 of the first ray alignment guide 700 results in the cuneiform cut guide 800 being secured in place until the user releases such releasable catch. The supports 750 of the second preferred embodiment are comprised of two protuberances extending from front and rear surfaces of the cut aperture 740 that interact with the positioning guide 810 that is comprised of two T-shaped protuberances that extend from front and rear sides of a body of the cuneiform cut guide 800, as well as a side surface of the cuneiform cut guide 800 that interacts with a side surface of the cut aperture 740. The cuneiform cut guide 800 is not limited to being connected to the first ray alignment guide 700 utilizing the described positioning guide 810 and the supports 750 and may be comprised of nearly any features and components that are able to secure the first ray alignment guide 700 and the cuneiform cut guide 800 such that the positioner 830 is positioned in the joint and the cut guide slot 840 is aligned for cutting and preparation of the medial cuneiform 1140 by defining the cuneiform cut plane 1140b in the medial cuneiform 1140.

In the preferred embodiment, an alignment outrigger 820 is attached to the top surface 815 of the body of the cuneiform cut guide 800 at its most medial aspect. The alignment outrigger 820 extends from the attachment point on the top surface 815 of the body laterally then turns approximately ninety degrees (90°) and extends distally and generally perpendicular to the cut guide slot 840 defining an alignment leg 822. The alignment leg 822 includes an alignment leg axis 822a that is spaced from and oriented generally parallel to the alignment axis 702 when the cuneiform cut guide 800 is attached to the first ray alignment guide 700 in the working configuration. The alignment leg 822 provides a visual indication to the user for aligning the first metatarsal 600 in a generally parallel orientation to the second metatarsal 100 (FIG. 11b) during a deformity correction process, although the procedure is not so limited and the medical professional may otherwise align the first metatarsal 600 relative to the second metatarsal 100, the medical cuneiform 1140 or nearly any other bones, bone portions or other anatomical features.

The cuneiform cut guide 800 may be further secured to the first ray alignment guide 700 utilizing an undercut or L-shaped feature within or extending from the top surface 730 that engages the alignment outrigger 820 when the cuneiform cut guide 800 is fully seated into the first ray alignment guide cut aperture 740. The first ray alignment guide 700 is not limited to including the undercut or L-shaped feature any other securement mechanisms or methods may be utilized to secure the cut guide 800 to the first ray alignment guide 700 in the working configuration, such as fasteners, clamping, force fit or other securement hardware or techniques. Release of the cuneiform cut guide 800 from the first ray alignment guide 800 is preferably achieved by slightly bending the alignment outrigger 820 away from the catch in the preferred embodiment. The positioner 830 that extends downwardly from the body of the cuneiform cut guide 800 has a geometry configured to generally fit within the TMT joint space and abut the head 1140a of the medial cuneiform 1140. The cut guide slot 840 is configured with a surface proximate and oriented generally parallel to the positioner 830. The cut guide slot 840 preferably has a geometry configured to accept the cutting blade 1900 of the bone saw for cutting the articular surface of the first metatarsal base 600b to thereby define the metatarsal cut plane 600c.

Referring to FIGS. 9-17b, in the second preferred embodiment the compressor-distractor assembly 900 includes the cam axle 940, the cam lever 920 having a cam lever handle 921, a cam lever center 930, and the compressor-distractor cam 910. The cam lever 920 is configured to attach to the cam axle 940 through the cam lever center 930. The cam lever center 930 is rotatably positioned in a cam lever center hole 923 with the cam lever center axis 931 aligned with a cam lever center axis 924 of the cam lever 920. The cam lever center 930 is configured to receive a cam axle head 940a of the cam axle 940 through a hole perpendicular to the cam lever center axis 931 such that the cam axle head 940a of the cam axle 940 does not pass through the cam lever center 930. The cam lever 920 includes a cam lever edge 922 having a cam-shaped circumference around the cam lever center axis 924. A retaining clip 950 is secured to a groove 941 at an end of the cam axle 940 opposite the cam axle head 940a preferably at a distal end of the cam axle 940. In the assembled configuration (FIG. 10), the cam axle 940 is positioned in the cam lever center 930, which is positioned in the cam lever center hole 923 of the cam lever 920 such that pivoting of the cam lever 920 causes the groove 941 and retaining clip 950 to move upwardly or downwardly relative to the compressor-distractor cam 910. The compressor-distractor assembly 900 is positioned between the first and second posts 780, 790 above the second metatarsal aperture 732 of the first ray alignment guide 700 and the distal end of the cam axle 940 extends through the axle hole 260 of the base scaffold 200 such that the retaining clip 950 is positioned at a bottom side of the axle hole 260. The first ray alignment guide 700 is slidably attached to the metatarsal base scaffold 200 when the cam lever handle 921 of the cam lever 920 is oriented generally horizontally. The retaining clip 950 is secured onto the groove 941 to thereby securing the compressor-distractor assembly 900 to the first ray alignment guide 700 and the metatarsal base scaffold 200. In operation of the preferred embodiment, a torque applied to the lever handle 921 about the cam axle 940 imparts a rotation of the cam lever 920, thereby causing a base surface of the compressor-distractor cam 910 to impart a force directed onto the first ray alignment guide 700 relative to an equal and opposite force applied to the metatarsal base scaffold through the hole 260, thereby locking the positions of the base scaffold 200, the first ray alignment guide 700 and the compressor-distractor assembly 900 relative to each other when the cam lever handle 921 is oriented in a generally vertical orientation. When the cam lever 920 is oriented in a generally horizontal orientation, the first ray alignment guide 700 is translatable relative to the base scaffold 200, guided by the guide surfaces 280, 281, 290, 291 of the base scaffold 200 and the sides and rails 710, 711, 720, 721 of the first ray alignment guide 700.

Figure 2:
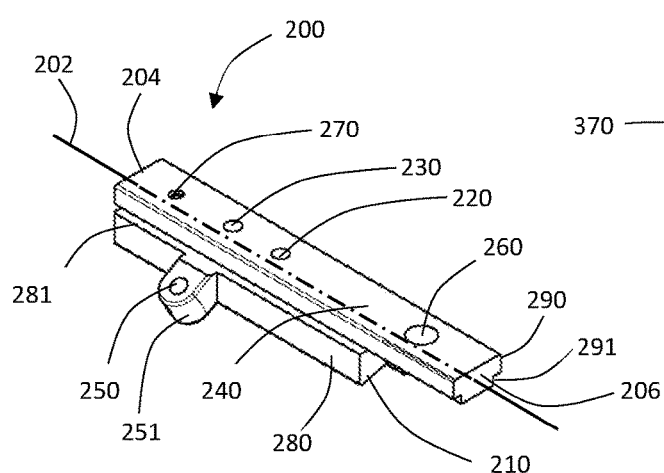
FIG. 2 is an isometric perspective view of a metatarsal base scaffold tool or instrument in accordance with a second preferred embodiment of the present invention.
Figure 3:
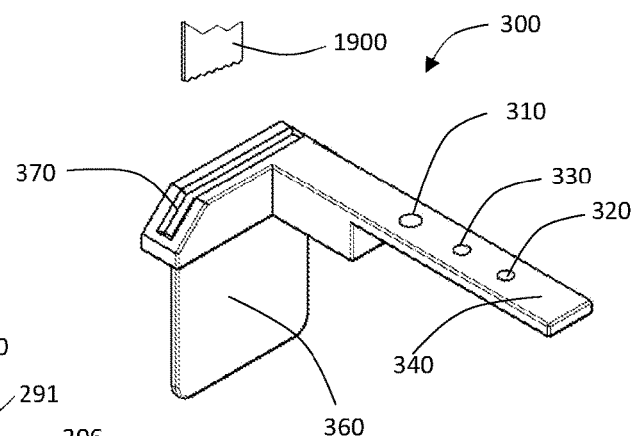
FIG. 3 is an isometric perspective view of a metatarsal base cut guide tool or instrument.
Figure 4:
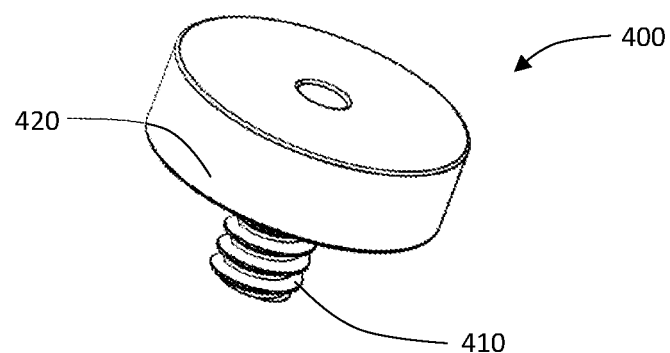
FIG. 4 is an isometric perspective view of a threaded attachment knob tool or instrument.
Figure 9:
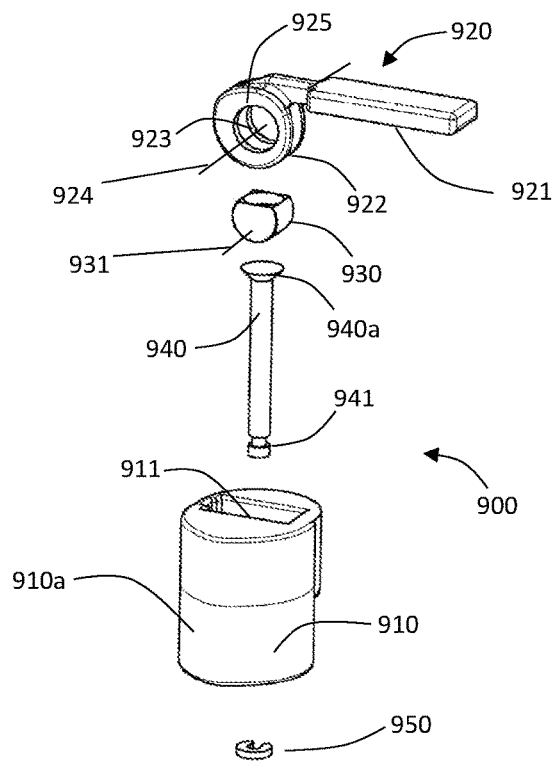
FIG. 9 is an isometric exploded view of a compressor-distractor assembly component.
Figure 10:
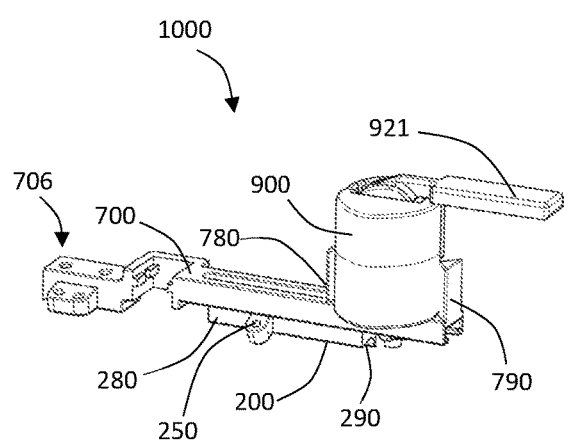
FIG. 10 is an isometric view of the compressor-distractor assembly component of FIG. 9 mounted to the first ray alignment guide of FIG. 7.
Figure 11A:
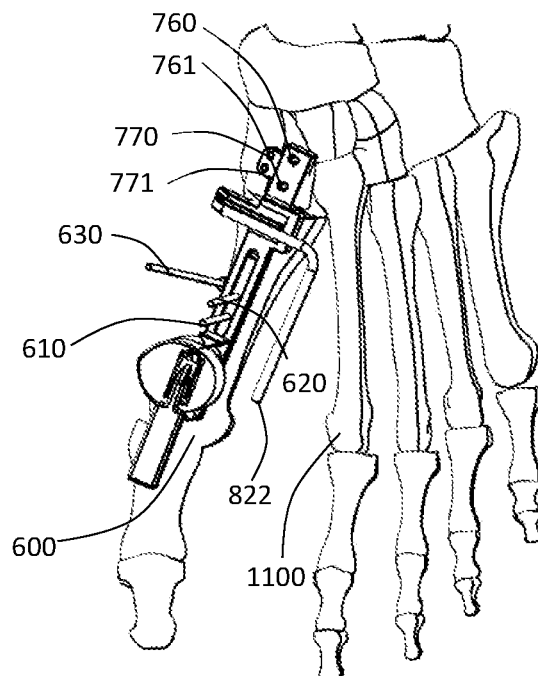
FIG. 11a is a dorsal view of a first ray multi-tool attached to a first metatarsal with bone pins through the metatarsal base scaffold component of FIG. 2 before correction of the first metatarsal alignment.
Figure 11B:
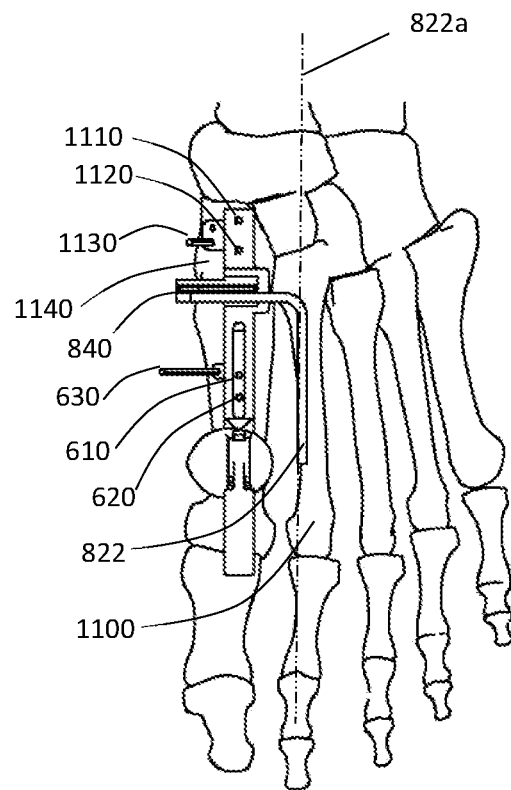
FIG. 11b is a dorsal view of the first ray multi-tool attached to the first metatarsal of FIG. 11a and a medial cuneiform with bone pins through the metatarsal base scaffold of FIG. 2 and first ray alignment guide of FIG. 7, respectively after alignment correction of the first metatarsal.
Figure 11C:
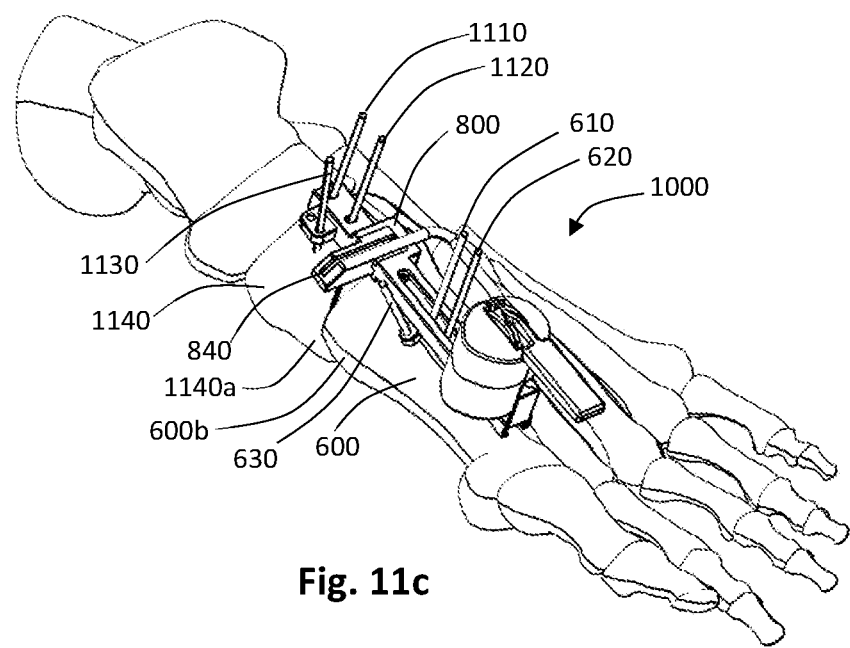
FIG. 11c is an isometric view of the first ray multi-tool attached to the first metatarsal and medial cuneiform of FIG. 11b.
Figure 14:
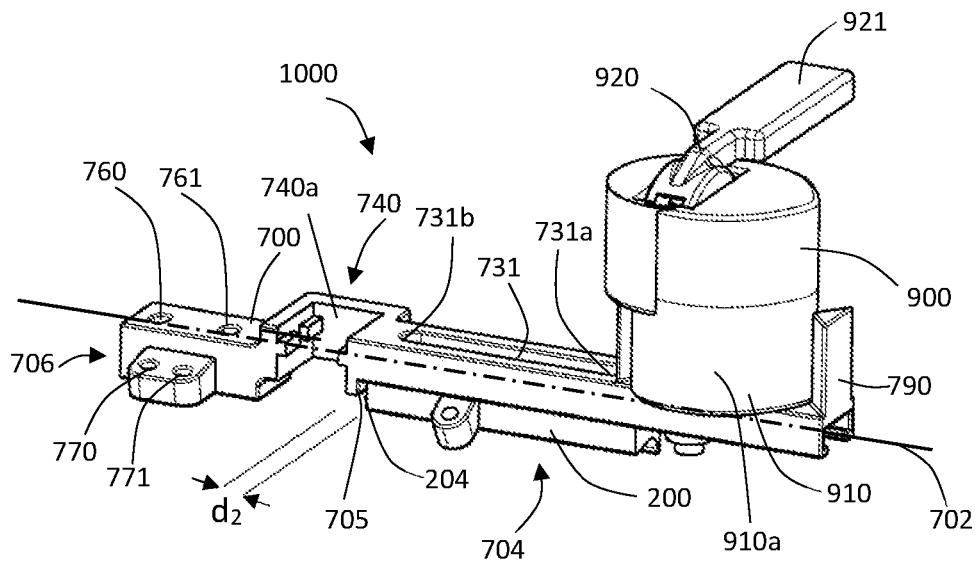
FIG. 14 is an isometric view of the first ray multi-tool of FIG. 10 in a compressed orientation.
Figure 15:
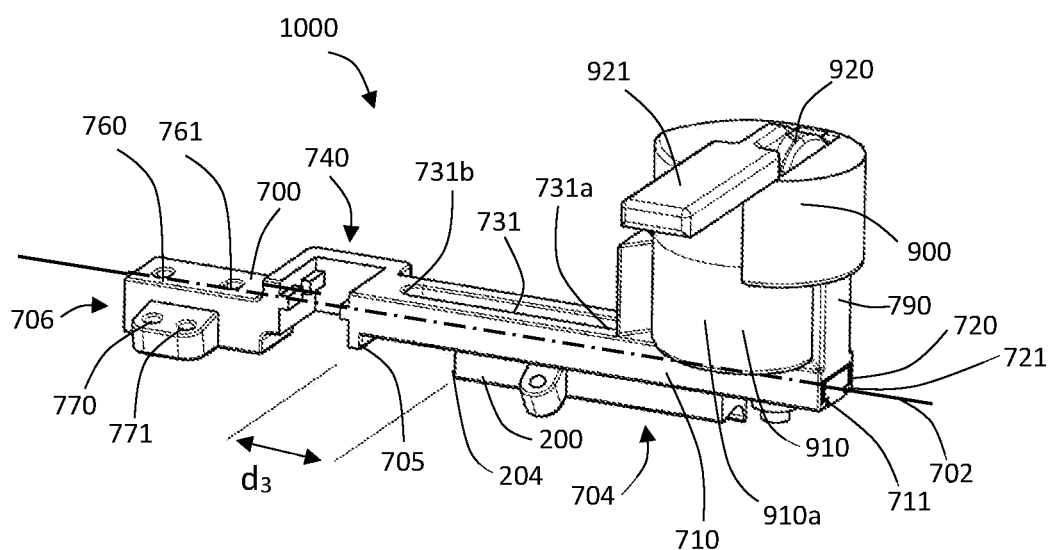
FIG. 15 is an isometric view of the first ray multi-tool of FIG. 10 in a distracted orientation.

In a further aspect of operation of the preferred embodiment of the compressor-distractor assembly 900, rotation of the cam lever 920 about the cam lever center 930 to a position such that the cam lever handle 921 is generally parallel to the cam axle 940 or generally in a vertical orientation imparts a force created by the cam edge 922 on the compressor-distractor cam 910 thereby imparting an upward directed force through the cam axle 940 to the retaining clip 950. The upward force of the retaining clip 950 is directed upon the metatarsal base scaffold 200 below the axle hole 260 and is countered by an equal and downward force imparted by the compressor-distractor cam 910 directed upon the top surface 730 of the first ray alignment guide 700. The forces between the metatarsal base scaffold 200, the compressor-distractor cam 910 and the first ray alignment guide 700 creates a frictional force generally preventing translational motion between the metatarsal base scaffold 200 and the first ray alignment guide 700. In the preferred embodiment, the construct combining the metatarsal base scaffold 200, the first ray alignment guide 700, and the attached compressor-distractor cam assembly 900 has a substantially equivalent function and operation to a preferred embodiment of the first ray multi-tool 1000 and is provided to the user pre-assembled in an instrument kit. It should be further understood in another preferred embodiment, the individual components, including the base scaffold 200, the first ray alignment guide 700 and the compressor-distractor assembly, as depicted in FIGS. 2, 7, and 9, may be provided to the user as removably attachable separate components of an instrument kit. It should also be understood that other embodiments are contemplated whereby any two of the individual components, including the base scaffold 200, the first ray alignment guide 700 and the compressor-distractor assembly, depicted in FIGS. 2, 7, and 9 are removably attached and provided to the user in an instrument kit.

Figure 5:
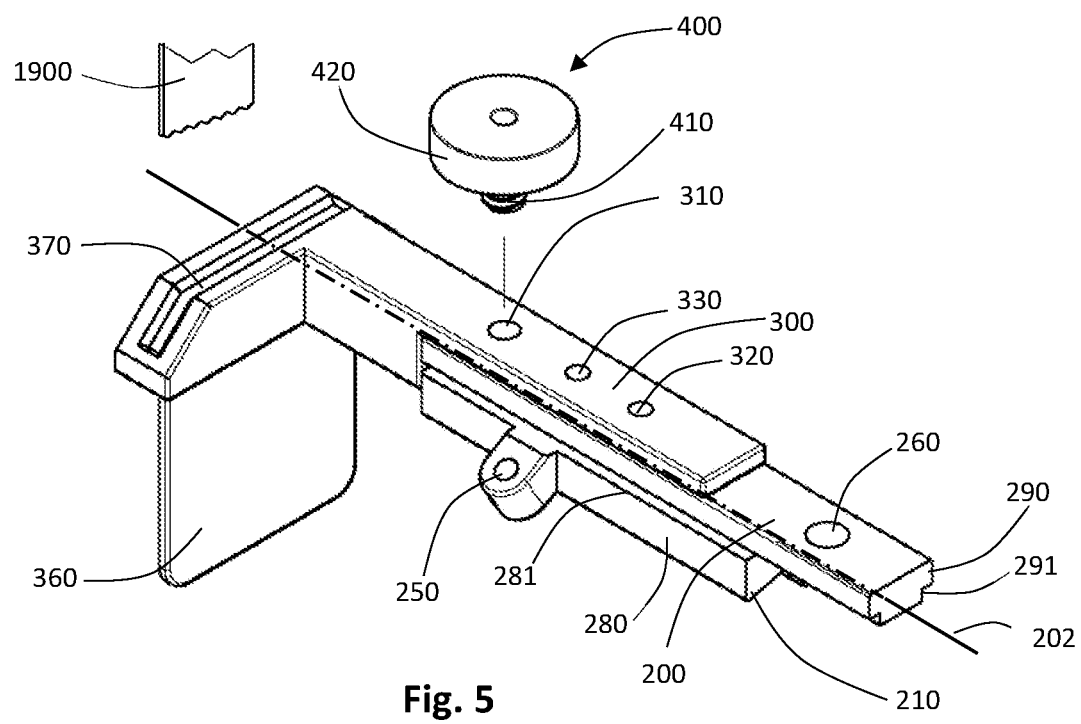
FIG. 5 is an isometric perspective view of the metatarsal base scaffold tool of FIG. 2 with the metatarsal base cut guide tool of FIG. 3 mounted thereon and the threaded attachment knob of FIG. 4 in a position aligned for insertion through the metatarsal base cut guide for removable attachment to the metatarsal base scaffold.

Referring to FIGS. 11a-16, in operation, the base scaffold 200 is mounted to the first metatarsal 600 such that the bone-contacting surface 210 is in engagement with a dorsal side of the first metatarsal 600 and the near side 204 is appropriately spaced from the TMT joint. The first ray alignment guide 700 is slidably mounted to the base scaffold 200 and the compressor-distractor assembly 900 is assembled to the first ray alignment guide 700. This assembly or the first ray multitool 1000 is shown in operation in FIGS. 11a-12b. The first ray multitool 1000 is preferably mounted to the first metatarsal 600 following removal of the metatarsal multi-tool or metatarsal cut guide 100 from the metatarsal but is not so limited and may be designed and configured for connection to the first metatarsal 600 utilizing the same base scaffold 200 following only removal of the metatarsal cut guide 300. After the articular surface of the first metatarsal base 600b of the first metatarsal 600 is removed by the cutting blade 1900 guided by the metatarsal cut guide 300 to define the metatarsal cut plane 600c, as depicted in FIG. 6 and associated operational description, the first ray multi-tool 1000 with the removably attached cuneiform cut guide 800 is placed over the first and second metatarsal bone pins 610, 620 which were inserted through the previously removed metatarsal multi-tool first and second holes 120, 130 of the multi-tool 100 or through the first and second scaffold holes 220, 230 and the first and second cut guide holes 320, 330, as shown in FIG. 5. The third bone pin 630 is preferably inserted through the angled hole 250 of the metatarsal base scaffold 200 of the first ray multi-tool 1000 to further secure the first ray multi-tool 1000 to the first metatarsal 600. The first metatarsal 600 is repositioned using the alignment outrigger 820, preferably by aligning the alignment leg 822 with the second metatarsal 1100, to guide the first metatarsal axis 600a of the first metatarsal 600 to an orientation generally parallel to the longitudinal axis of the second metatarsal 1100 (FIG. 11b). The user may also impart a rotation about the first metatarsal axis 600a of the first metatarsal 600 to correct any rotational mis-alignment. In the preferred embodiment, the cutting blade 1900 of a bone saw is inserted into the cuneiform cut guide slot 840 and the articular surface of the head 1140a of the medial cuneiform 1140 is removed and prepared thereby defining the cuneiform cut plane 1140b. Once a satisfactory orientation of the first metatarsal 600 or orientation of the first metatarsal 600 to the second metatarsal 1100 is attained, first, second and third cuneiform bone pins 1110, 1120, 1130 are preferably inserted into the first and second cuneiform holes 760, 761, and either of the first or second angled holes 770, 771 on the cuneiform side 706 of the first ray alignment guide 700 to secure the first ray multi-tool 1000 to the medial cuneiform 1140.

The first ray multi-tool 1000 is attached to the medial cuneiform 1140 and the first metatarsal 600 although the base scaffold 200 is translatable relative to the first ray alignment guide 700 until the compressor-distractor assembly 900 is actuated to the locked configuration with the cam lever handle 921 oriented generally vertically. The first ray multi-tool 1000 is preferably attached to the medial cuneiform 1140 following the operational steps of correcting the alignment of the first metatarsal 600 further followed by cutting and removing the articular surface of the medial cuneiform head 600b to define the metatarsal cut plane 600c, as described above. Operationally, the cuneiform cut guide 800 is preferably removed from the first ray alignment guide 700 following the operational step of cutting the articular surface of the medial cuneiform head 60b, although the procedure is not so limited, and the cuneiform cut guide 800 may remain connected to the first ray alignment guide 700 for portions of the remaining procedure. The first and second cuneiform bone pins 1110, 1120 are preferably inserted into the lateral aspect of the tapered first and second cuneiform holes 760, 761 of the first ray alignment guide 700 and into the medial cuneiform 1140. The third cuneiform bone pin 1130 is may also be inserted into the oblique or angled first or second angled holes 771 of the first ray alignment guide 700 to further secure the first ray alignment guide 700 into the medial cuneiform 1140. Additional rotation may subsequently be imparted about the first metatarsal axis 600a of the first metatarsal 600 by removing the third cuneiform bone pin 1130 and rotating the first ray multi-tool 1000 such that the first and second cuneiform bone pins 1110, 1120 are displaced toward the medial aspect of the tapered first and second cuneiform holes 760, 770. Upon achieving the desired amount of rotation, the user then reinserts the third cuneiform bone pin 1130 into the first or second angled holes 770, 771, thereby again securing the first ray multi-tool 1000 to the medial cuneiform 1140 from displacement in any direction relative to the medial cuneiform 1140.

The first ray multi-tool 1000 is configured such that the compressor-distractor assembly 900 is oriented in a rotational position placing the first ray alignment guide 700 in a generally central position within a displacement boundary defined by a length of the first metatarsal aperture 731 between the first and second sides 731a, 731b. In the supplied configuration when the user unpackages the first ray multi-tool 1000, the first and second scaffold holes 220, 230 are positioned generally centrally relative to the first metatarsal aperture 731 along the alignment axis 702 of the first ray alignment guide 700. A first or neutral distance d1 (FIG. 13) is shown representing the neutral distance d1 between the near side 204 of the metatarsal base scaffold 200 and a proximal lip 705 of the first ray alignment guide 700 that extends downwardly from the first ray alignment guide 700 near an intersection between the cut aperture 740 and the metatarsal side 704. The first ray multi-tool 1000 is generally supplied in this neutral position when provided to the user. In the supplied configuration, the cam lever handle 921 is oriented generally parallel to the alignment axis 702 and horizontal or parallel to the top surface 730.

The first ray multi-tool 1000 may be configured such that the compressor-distractor component 900 is oriented in a rotational position placing the first ray alignment guide 700 in a generally distally translated position or a fully compressed position (FIG. 14), respective to the metatarsal anatomy, within a displacement boundary relative to the base scaffold 200 along the alignment axis 702 of the first ray alignment guide 700. A second distance d2 in the distally translated position or the fully compressed position is less than the first distance d1. In operation, the second distance d2 represents a movement of the metatarsal base scaffold 200 component toward the TMT joint translating to joint compression in clinical practice. In the distally translated or fully compressed position, the second distance d2 may be zero such that the near side 204 is positioned against the proximal lip 705 and the first and second scaffold holes 220, 230 are positioned proximate the second side 731b of the first metatarsal aperture 731. The first and second metatarsal bone pins 610, 620 may also be positioned proximate the second side 731b when the first ray multi-tool 1000 is connected to the first metatarsal 600 and is in the distally translated or fully compressed position. In the distally translated or fully compressed position, the cam lever handle 921 is pivoted generally ninety degrees (90°) from the orientation parallel to the alignment axis 702 toward the second side 720 of the first ray alignment guide 700. The cam surface 910a of the compressor-distractor cam 910 contacts the first and/or second posts 780, 790 to urge the first ray alignment guide 700 relative to the base scaffold 200 to this distally translated or fully compressed position when the compressor-distractor cam 910 is pivoted to this orientation by the cam lever handle 921.

The first ray multi-tool 1000 may also be configured such that the compressor-distractor assembly 900, specifically the compressor-distractor cam 910, is oriented in a rotational position placing the first ray alignment guide 700 in a generally proximally translated or fully distracted position (FIG. 15), respective to the metatarsal anatomy, within a displacement boundary relative to the base scaffold 200 along the alignment axis 702. In the fully distracted position, the compressor-distractor cam 910 is pivoted relative to the first ray alignment guide 700, specifically the first and second posts 780, 790, such that the cam lever handle 921 is oriented generally perpendicular relative to the alignment axis 702 and at the first side 710. In this fully distracted position, the near side 204 of the base scaffold 200 is spaced at its greatest distance from the proximal lip 705 of the first ray alignment guide 700. A third or distracted distance d3 is defined in the fully distracted position, wherein the third distance d3 is greater than the first and second distances d1, d2. In operation, the third distance d3 represents a movement of the metatarsal base scaffold 200 component away from the TMT joint translating to joint distraction in clinical practice. The fully distracted position d3 is not limited to the described and shown orientation of the compressor-distractor cam 910 and the cam lever handle 921 and the compressor-distractor cam 910 may be oriented at nearly any rotational position relative to the first and second posts 780, 790 such that the near side 204 is spaced at its maximum distance relative to the proximal lip 705.

Figure 16:
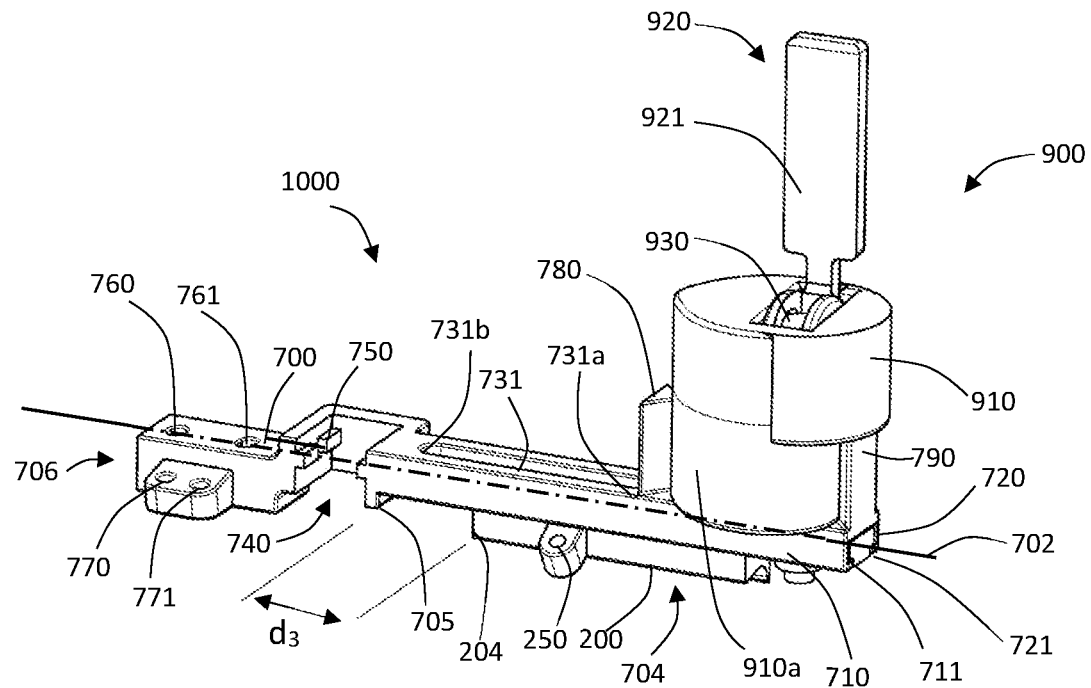
FIG. 16 is an isometric view of the first ray multi-tool of FIG. 10 in a distracted orientation with the second cam lever in a locked position.

In operation the first ray multi-tool 1000 is preferably delivered in the neutral position (FIG. 13), with the first and second scaffold holes 220, 230 generally centered relative to the first metatarsal aperture 731, such that the first ray alignment guide 700 may be translated in both directions with respect to the base scaffold 200. The compressor-distractor cam 900 may be pivoted such that the cam lever handle 921 is rotationally oriented in a position causing the first ray multi-tool 100 to be configured in or toward the fully distracted position by pivoting the compressor distractor cam 910 and the cam lever handle 921 toward the first side 710 such that the cam lever handle 921 is oriented generally perpendicular to the alignment axis 702. In any of the positions at and between the fully compressed and the fully distracted positions the cam lever 920 may rotated about the cam lever center axis 931 to a position such that the longitudinal axis of the cam lever handle 921 is generally parallel to the cam axle 940 (FIG. 16). When the cam lever handle 921 is in this generally vertical configuration, a resulting force created by the cam lever 920 and the retaining clip 950 between the metatarsal base scaffold 200, the compressor-distractor cam 910 and the first ray alignment guide 700 creates a frictional force generally locking the position of the metatarsal base scaffold 200 relative to the first ray alignment guide 700. It should be generally understood and appreciated by one having ordinary skill in the art based on a review of the present disclosure that the locking action imparted by rotating the cam lever 920 causes the associated locking action between the metatarsal base scaffold 200 and the first ray alignment guide 700 for any rotational orientation of the compressor-distractor component 900. Thereby and correspondingly, in a functional application whereby the base scaffold 200 is attached to the first metatarsal 600 and the first ray alignment guide 700 is attached to the medial cuneiform 1140, the user may fix the joint space between the medial cuneiform 1140 and the first metatarsal 600 in a compressed or distracted state as well as a plurality of joint gap spacings therebetween. The first ray multi-tool 1000 is not limited to locking when the cam lever handle 921 is in the vertical orientation and release when the cam lever handle 921 is generally in the horizontal orientation and may be otherwise designed and configured to facilitate release and locking when the cam lever handle 921 is in alternative orientations. In addition, the first ray multi-tool 1000 is not limited to locking the assembly by operation of the cam lever handle 921 and the assembly may be otherwise designed and configured for locking and release, such as by utilizing fasteners, clamps or other features that facilitate locking of the position of the first ray alignment guide 700 relative to the base scaffold 200 and release for generally linear translation of the first ray alignment guide 700 relative to the base scaffold 200.

Figure 17A:
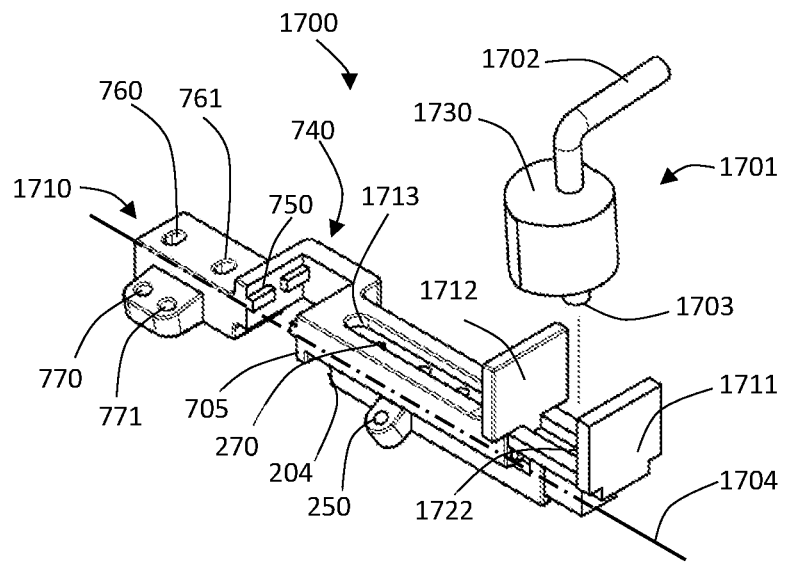
FIG. 17a is an isometric view of a second aspect of the first ray alignment guide of FIG. 7 removably mounted to a second aspect of the metatarsal base scaffold of FIG. 2 configured to receive a non-locking compressor-distractor component.
Figure 17B:
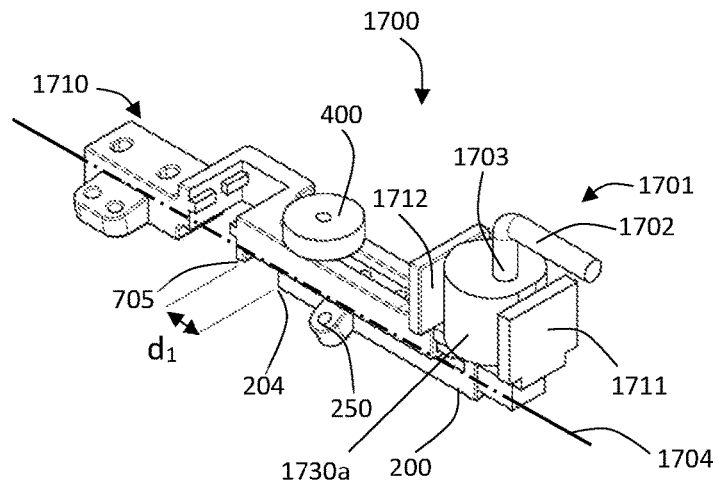
FIG. 17b is an isometric view of the first ray alignment guide and metatarsal base scaffold of FIG. 17a with the compressor-distractor component of FIG. 17a in a distracted position with the threaded attachment knob of FIG. 4 configured to lock the distracted orientation.

Referring to FIGS. 17*a* and 17*b*, in an alternative third preferred embodiment, a first ray multi-tool 1700 having similar features relative to the first ray multi-tool 1000 of the third preferred embodiment is shown with the same reference numbers utilized to identify similar features and the differences between the third preferred embodiment and the alternative third preferred embodiment described below with different reference numbers utilized to identify the different features. The alternative third preferred first ray multi-tool 1700 is configured to removably attach to a first metatarsal 600 and a medial cuneiform 1140 to facilitate alignment of the bones but is not so limited and may be design and configured for correcting mis-alignment of other bones and/or bone segments or for compression or distraction of other bones or bone segments. The alternative third preferred first ray multi-tool 1700 includes an alternative compressor-distractor assembly 1701 with a compressor-distractor cam 1730 with a cam surface 1730*a*, a cam axle 1703 extending through a hole in the compressor-distractor cam 1730 and a cam lever 1702 that extends generally perpendicularly relative to the cam axle 1703 at a top of the compressor-distractor cam 1730. The cam axle 1703 and cam lever 1702 are fixed to the compressor-distractor cam 1730. An alternative first ray alignment guide 1710 of the alternative third preferred embodiment is assembled with the base scaffold 200, although the base scaffold 200 may be modified to accommodate the configuration and function of the alternative third preferred first ray alignment guide 1710 or other components of the alternative third preferred first ray multi-tool 1700. The first ray alignment guide 1710 includes relatively sheet-like or plate-like first and second posts 1711, 1712 that are oriented generally perpendicular to the alignment axis 1704 of the first ray alignment guide 1710. The alternative third preferred first and second posts 1711, 1712 are spaced apart at a distance corresponding to a profile of the compressor-distractor cam 1730 and may contact the cam surface 1730*a*. The threaded attachment knob 400 is configured to thread into the threaded hole 270 of the base scaffold 200 through a first metatarsal aperture 1713 of the first ray alignment guide 1710 that extends generally parallel to the alignment axis 1704. A bottom of the cam axle 1703 extends through a second metatarsal aperture 1705 of the first ray alignment guide 1710 of the alternative third preferred embodiment and extends through the threaded hole 270 of the base scaffold 200 in an assembled configuration.

In operation, the TMT joint is prepared and the alternative third preferred embodiment of the first ray multi-tool 1700 is mounted to the first metatarsal 600 and the medial cuneiform 1140, preferably in the neutral position (FIG. 17*b*). A pivoting force is applied to the cam lever 1702 that imparts a torque about the axis of the cam axle 1703 causing the compressor-distractor cam 1730 to rotate thereby imparting a force against the first and/or second posts 1711, 1712 by the cam surface 1730*a* opposed by an equal and opposite force created by the interface between the cam axle 1703 and the base scaffold hole 1722. The force applied to the first and/or second posts 1711, 1712 by the cam surface 1730a of the compressor-distractor assembly 1701 during pivoting of the cam axle 1703 causes a translation of the metatarsal base scaffold 200 relative to the first ray alignment guide 1710, generally along the alignment axis 1704 of the first ray alignment guide 1710. In a functional application whereby the base scaffold 200 is attached to the first metatarsal 600 and the first ray alignment guide 1710 is attached to the medial cuneiform, the translation of the base scaffold 200 corresponds to a clinical translation of the first metatarsal 600 toward or away from the medial cuneiform 1140, thereby resulting in compression or distraction. When a desired amount of translation is achieved, a user turns the attachment knob 400 causing it to insert further into the threaded hole 270 thereby compressing the first ray alignment guide 1710 against the base scaffold 200, restricting further translation of the base scaffold 200 relative to the first ray alignment guide 1720 of the alternative third preferred embodiment and locking the position of the base scaffold 200 relative to the first ray alignment guide 1710. The alternative third preferred first ray multi-tool 1700 is not limited to locking translation of the base scaffold 200 to the first ray alignment guide 1720 with the attachment know 400 and alternative locking mechanisms and methods may be utilized, such as alternative fasteners, clamping or other mechanisms or methods to generally secure the base scaffold 200 to the first ray alignment guide 1720 when the associated bones or bone segments are oriented and spaces at desired positions relative to each other. The orientation of the first metatarsal 600 relative to the medial cuneiform 1140 and the second metatarsal 1100 utilizing methods similar to those described above, including use of the cuneiform cut guide 800 with the alignment leg 820 and the first preferred cut guide 100 or the assembled base scaffold 200 with the metatarsal cut guide 300 of the second preferred embodiment to prepare the TMT joint.

The alternative third preferred first ray multi-tool 1700 may include the same base scaffold 200 utilized in the same procedure as is utilized with the metatarsal cut guide 300 or may be configured such that the base scaffold 200 is comprised of first and second base scaffolds 200 that are provided with the cut guide 300 and the first ray multi-tool 1700 in a kit to perform a procedure as described herein. The first and second base scaffolds in the kit may have the same or similar features with the first base scaffold 200 utilized with the metatarsal cut guide 300 and the second base scaffold 200 utilized with the first ray multi-tool 1700. The base scaffold 200 of the additional preferred embodiments described herein may be similarly designed and configured such that multiple base scaffolds 200 are provided to the user in a kit or individually for connection to the first metatarsal 600 or another bone for manipulation of the first metatarsal 600 or other bone. The base scaffold 200 may also be provided in the kit pre-assembled with other components, such as the metatarsal cut guide 300, the first ray multi-tool 1700, other first ray multi-tools described herein or with other components as would be apparent to one having ordinary skill in the art based on reviewing the present disclosure.

Figure 18:
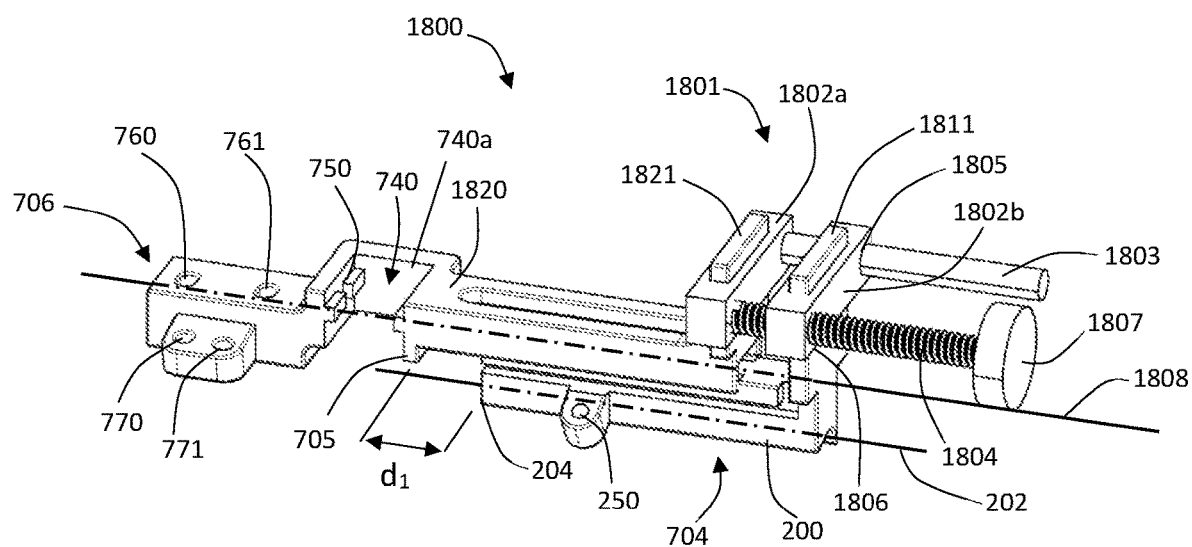
FIG. 18 is an isometric perspective view of a fourth preferred embodiment of a first ray alignment guide slidably mounted to a fourth preferred embodiment of a metatarsal base scaffold with a threaded screw compressor-distractor component mounted to the first ray alignment guide and metatarsal base scaffold.

Referring to FIG. 18, in fourth preferred embodiment, a first ray multi-tool 1800 having similar features relative to the first ray multi-tools 1000, 1700 of the third alternative and third preferred embodiments is shown with the same reference numbers utilized to identify similar features and the differences between the third or alternative third preferred embodiments and the fourth preferred embodiment described below with different reference numbers utilized to identify the different features of the fourth preferred embodiment of the first ray multi-tool 1800. The fourth preferred first ray multi-tool 1800 includes an alternative compressor-distractor assembly 1801 that is removably attach to a base scaffold 200 with a base tab 1811 and an alternative first ray alignment guide 1820 with an alignment guide tab 1821. The base tab 1811 of the base scaffold 200 and the alignment guide tab 1821 of the first ray alignment guide 1820 are preferably proximate and separated by a distance bounded by the translation range of the slidable engagement between the base scaffold 200 and the first ray alignment guide 1820 in an assembled configuration. The base tab 1811 preferably extends generally perpendicularly and upwardly relative to the scaffold axis 202 and the alignment guide tab 1821 preferably extends generally perpendicularly and upwardly relative to an alignment axis 1808 of the first ray alignment guide 1820. The compressor-distractor assembly 1801 includes a first socket 1802a mountable on the alignment guide tab 1821 and a second socket 1802b mountable on the base tab 1811. The first and second sockets 1802a, 1802b are configured to slide over the alignment guide tab 1821 and the base tab 1811, respectively. A guide rail 1803 is fixed to a first socket 1802a and is oriented perpendicular to the first ray alignment guide tab 1821 and generally parallel to the scaffold axis 202 and the alignment axis 1808 in the assembled configuration. A threaded rod 1804 is fixed to the first socket 1802a at an adjacent side of the first socket 1802a from the guide rail 1830 such that rotation of the threaded rod 1804 about a longitudinal axis of threaded rod 1804 is allowed but translation along the longitudinal axis relative to the first socket 1802a is generally not. The threaded rod 1804 is oriented generally parallel to guide rail 1803, as well as the alignment axis 1808 and the scaffold axis 202. The second socket 1802 includes a socket hole 1805 through which the guide rail 1803 extends and is configured such that the second socket 1802b slides along the long axis of the guide rail 1803 during operation of the threaded rod 1804. The second socket 1802b also includes a threaded hole 1806 through which the threaded rod 1804 is threadably inserted for driving the movement of the first and second sockets 1802a, 1802b relative to each other. A compressor-distractor knob 1807 is preferably fixed to a distal end of threaded rod 1804 and is configured to rotate the threaded rod 1804 during operation, although the threaded rod 1804 is not limited to including the compressor-distractor knob 1807 and may include a handle, tab, precision driven motor or other mechanism or method that facilitates rotation of the threaded rod 1804 during use.

In operation, turning the compressor-distractor knob 1807 turns the threaded rod 1804, thereby driving the second socket 1802b relative to the first socket 1802a along the longitudinal axis of the guide rail 1803, generally parallel to the scaffold axis 202 and the alignment axis 1808. In a preferred embodiment, a counterclockwise rotation of the compressor-distractor knob 1807 results in translation the second socket 1802b toward the first socket 1801a thereby causing the base scaffold 200 to translate along the scaffold axis 202 and generally parallel to the alignment axis 1808 of the first ray alignment guide 1820 in a direction corresponding to moving the first metatarsal 600 toward the medial cuneiform 1140 or compression of the bones or bone segments toward each other. In contrast, a clockwise rotation of compressor-distractor knob 1807 results in translation of the second socket 1802b away the first socket 1802a thereby causing the base scaffold 200 to translate along the alignment axis 1808 of the first ray alignment guide 1820 in a direction corresponding to moving the first metatarsal 600 away from the medial cuneiform 1140 or distraction of the bones or bone segments away from each other. The fourth preferred first ray multi-tool 1800 may also be utilized to align the first metatarsal 600 and medial cuneiform 1140 relative to each other and/or relative to the second metatarsal 1100 and to prepare the TMT joint in the same or similar manner as the previously described embodiments, including use of the cuneiform cut guide 800, the first preferred cut guide 100 and/or the assembled base scaffold 200 and the metatarsal cut guide 300.

The first ray multi-tool 1800 of the fourth preferred embodiment may be utilize as an independent assembly, including the base scaffold 200 and the first ray alignment guide 1820 without any additional components being utilized to perform the procedure. The base tab 1811 of the base scaffold 200 and the alignment guide tab 1821 of the first ray alignment guide 1820 provide a rigid surface against which a user can impart external force to push the base tab 1811 of the base scaffold 200 toward or away from the alignment guide tab 1821 of the first ray alignment guide 1820 thereby creating the associated relative motion between the base scaffold 200 and the first ray alignment guide 1820 and the associated compression or distraction at the TMT joint. In this generally manual configuration, the threaded rod 1804 and the threaded hole 1806 are not incorporated into the compressor-distractor assembly 1802 and the compressor-distractor assembly 1802 may or may not incorporate the guide rail 1803 and the socket hole 1805 or may include alternative or additional guiding features. The attachment knob 400 and base scaffold hole 200 utilized with the alternative third preferred first ray multi-tool 1700 may be incorporated within the fourth preferred embodiment of the first ray multi-tool 1800 of FIG. 18, as would be apparent to one having ordinary skill in the art based on a review of the present disclosure. When a desired amount of compression or distraction is achieved, a user may turn the attachment knob 400 in a tightening direction, thereby causing the attachment knob 400 to insert further into the threaded hole 270 to compress the first ray alignment guide 1820 against the base scaffold 200. Tightening the attachment knob 400 into the threaded hole 270 to an adequate pressure results in locking further translation of the first ray alignment guide 1820 relative to the base scaffold 200, thereby fixing the position of the base scaffold 200 relative to the first ray alignment guide 1820.

Figure 19:
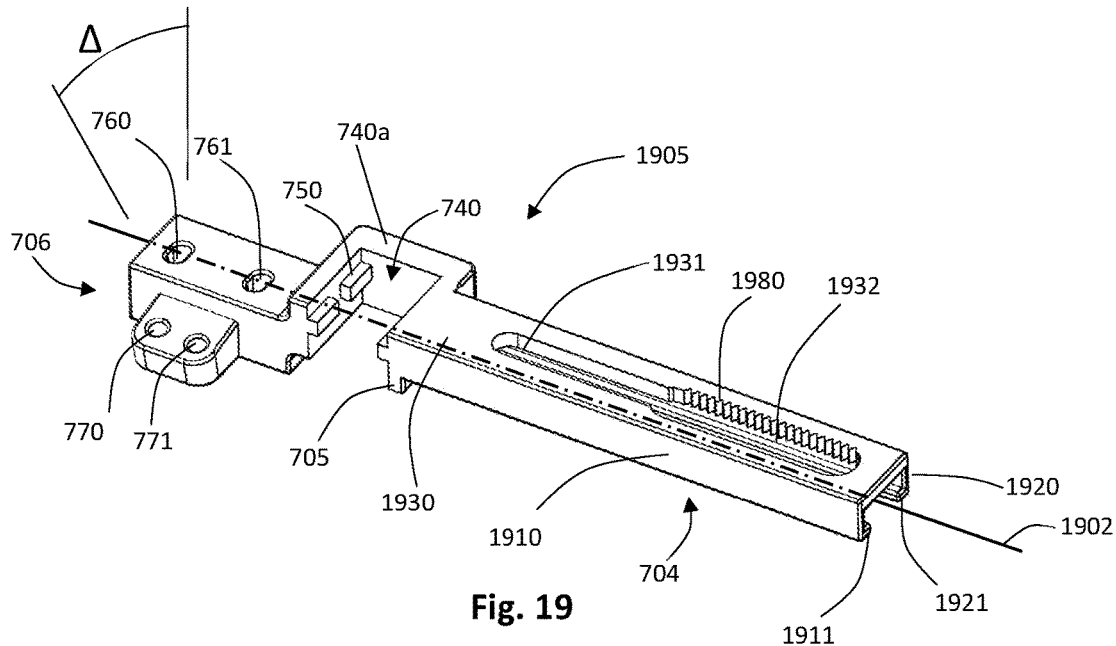
FIG. 19 is an isometric perspective view of a first ray alignment guide in accordance with a fifth preferred embodiment with a rack along a compressor-distractor slot for engaging with a pinion compressor-distractor drive assembly.
Figures 20A, 20B:
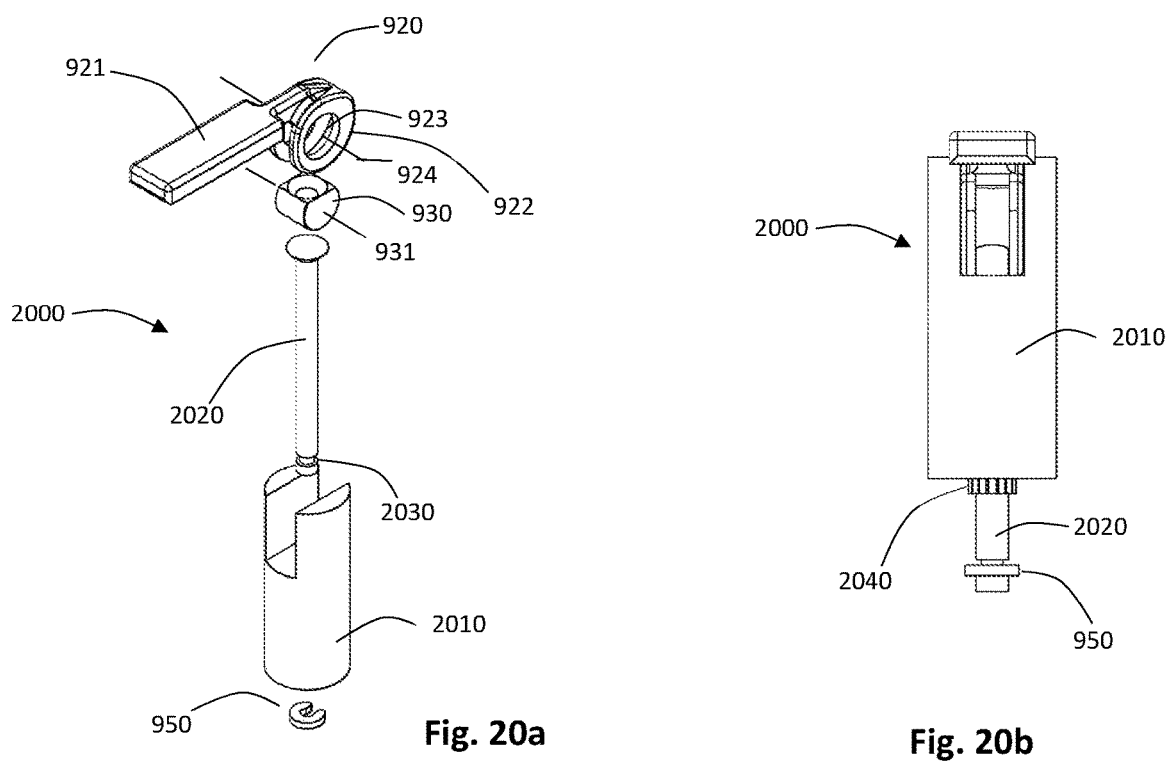
Figure 21:
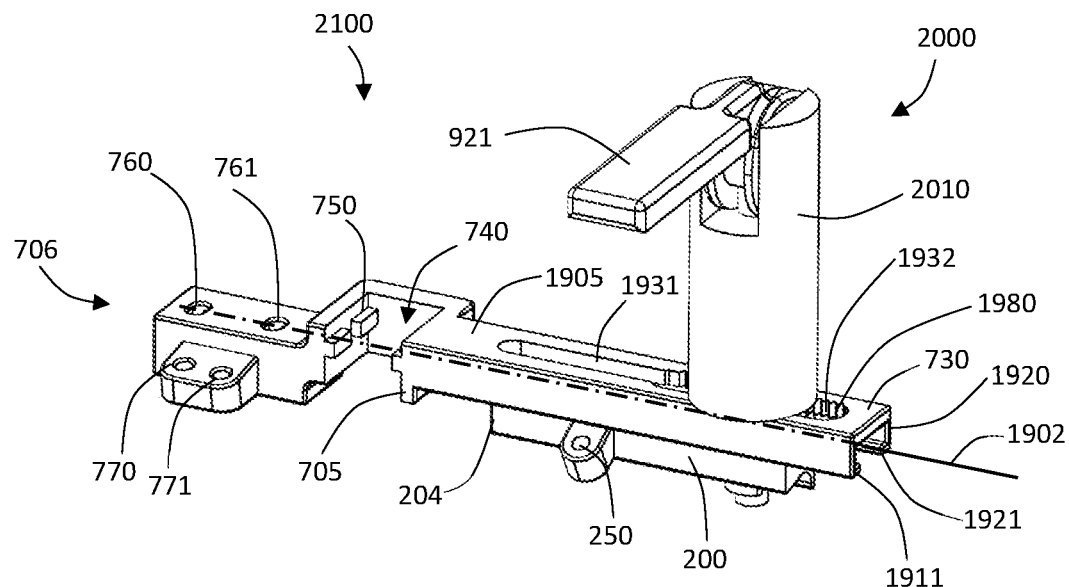
Figure 22A:
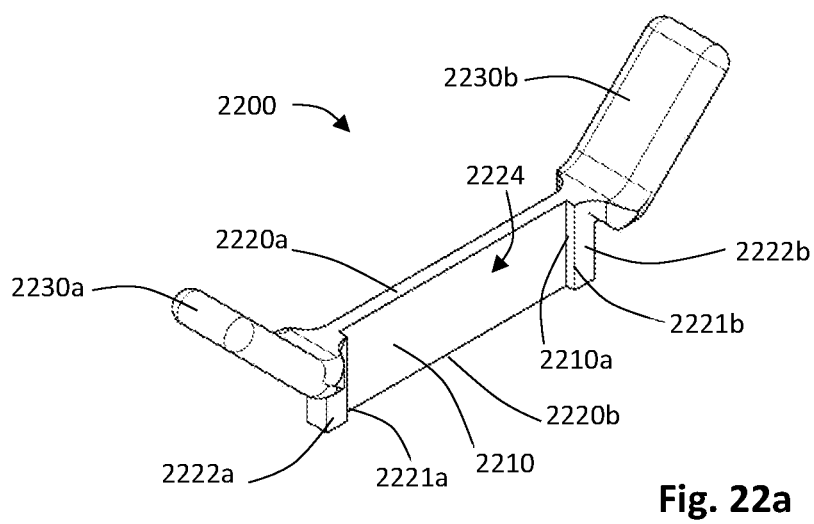
FIG. 22a is an isometric perspective view of a cut guide insert that may be utilized with any of the preferred cut guides described herein.
Figure 22B:
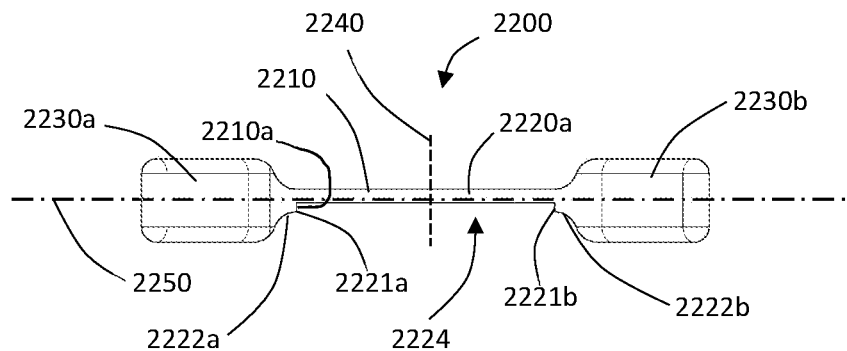
Figure 23:
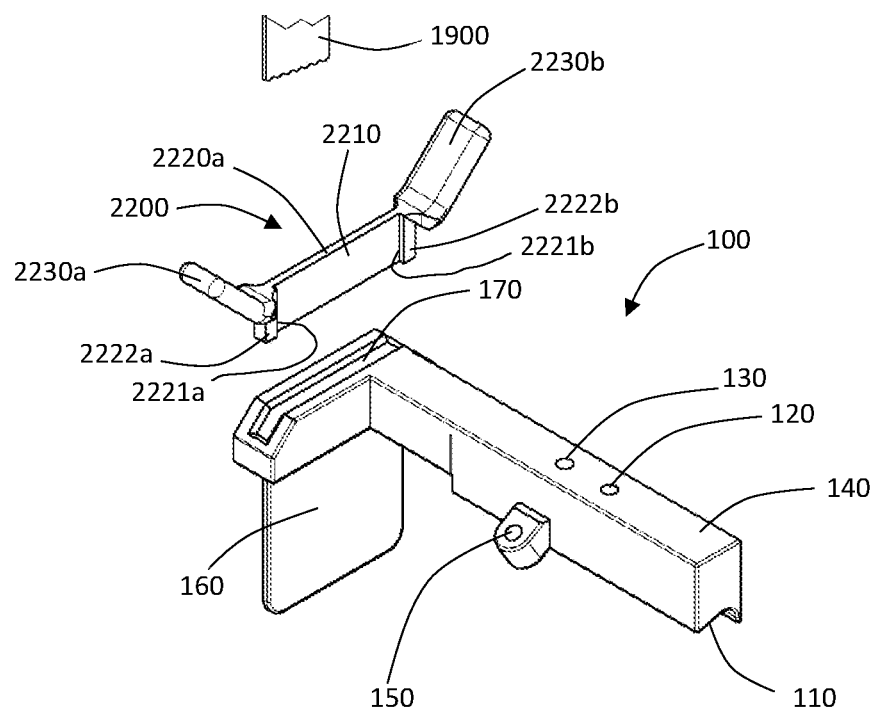
FIG. 23 is an isometric perspective view of the cut guide insert of FIG. 22a aligned above the first preferred metatarsal multi-tool of FIG. 1.
Figure 25:
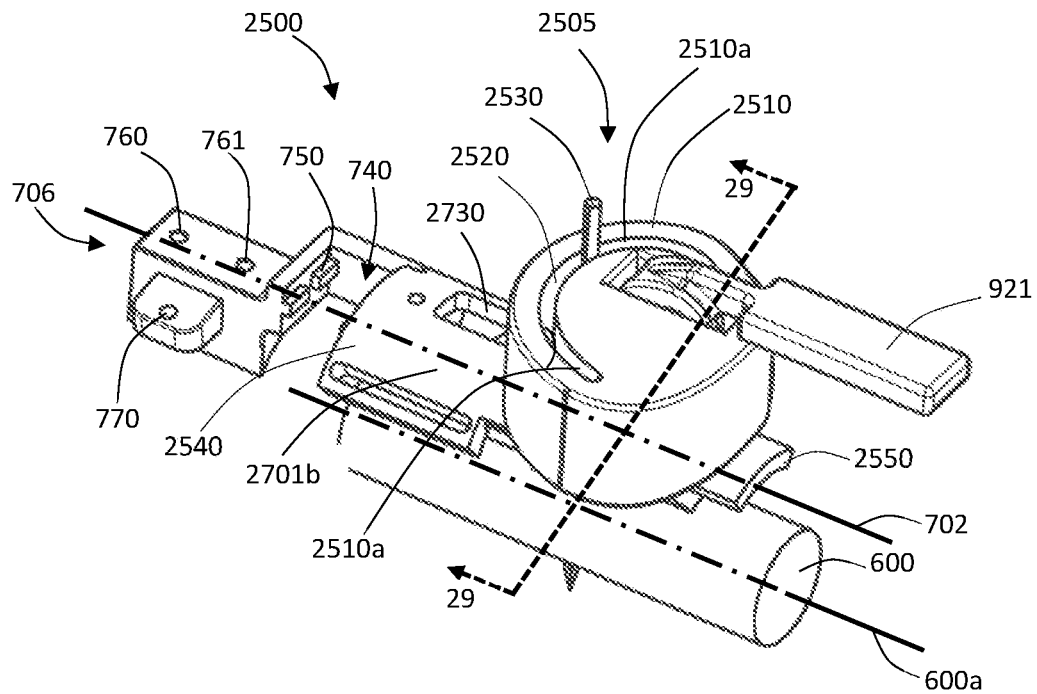
FIG. 25 is an isometric perspective view of a first ray multi-tool in accordance with a sixth preferred embodiment mounted to a first metatarsal, wherein the sixth preferred first ray multi-tool may comprise a portion of a kit for adjusting a first metatarsal relative to a medial cuneiform or other bones including a first ray alignment guide, a compressor-distractor assembly, a base scaffold and a rotation insert assembled and mounted to a bone, such as a first metatarsal in accordance with the sixth preferred embodiment of the present invention.
Figure 26:
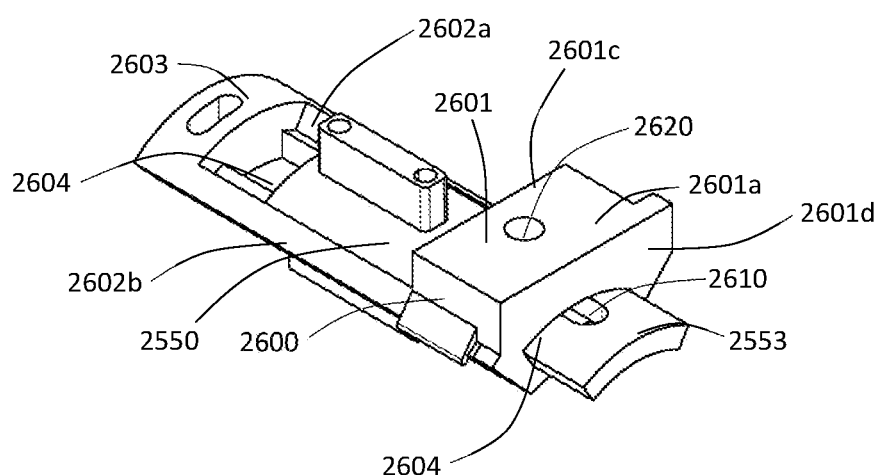
FIG. 26 is an isometric perspective view of the base scaffold assembled with the rotation insert of the first ray multi-tool of FIG. 25.
Figure 27:
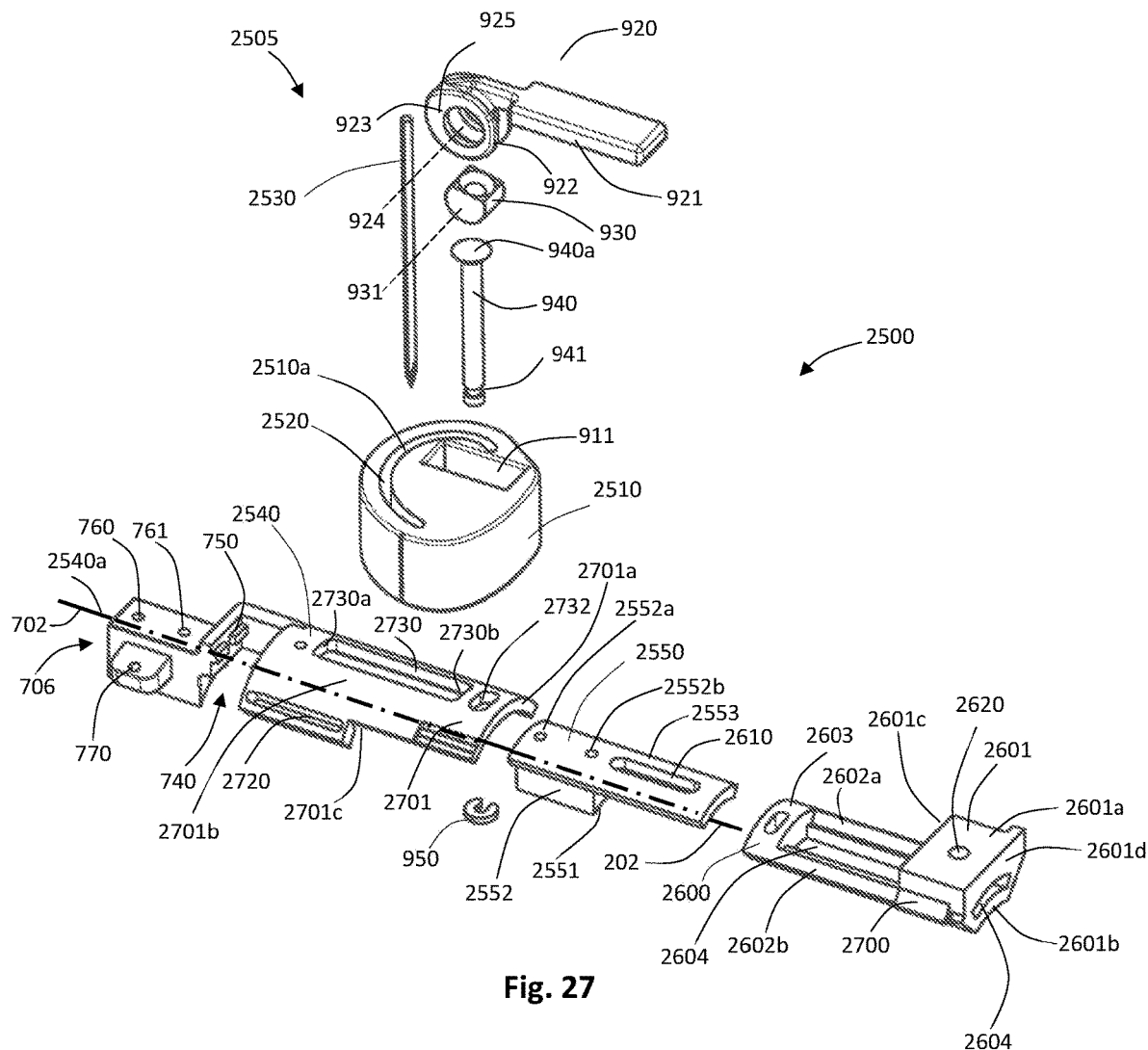
FIG. 27 is an isometric perspective exploded view of the first ray multi-tool of FIG. 25.

Referring to FIGS. 19-21, in a fifth preferred embodiment, a first ray multi-tool 2100 having similar features relative to the first ray multi-tools 1000, 1700, 1800 of the third, third alternative and fourth preferred embodiments is shown with the same reference numbers utilized to identify similar features and the differences between the third, third alternative, and fourth preferred embodiments and the fifth preferred embodiment are described below with different reference numbers utilized to identify the different features of the fourth preferred embodiment of the first ray multi-tool 2100. The first ray multi-tool 2100 of the fifth preferred embodiment includes the base scaffold 200, a first ray alignment guide 1905, and a compressor-distractor assembly 2000. The first ray alignment guide 1905 includes first and second sides 1910, 1920 that extend generally downwardly and perpendicular to a top surface 1930 at the metatarsal side 704. The first and second sides 1910, 1920 are configured to abut first and second sides 210, 220 of the base scaffold 200 in an assembled configuration. The first ray alignment guide 1905 also includes first and second rails 1911, 1921 that are configured for slidable engagement with first and second slots 281, 291 of the base scaffold 200 in the assembled configuration. A first metatarsal aperture 1931 is defined in the first ray alignment guide 1905 in the metatarsal side 704 and extends generally parallel to the alignment axis 1902. The first metatarsal aperture 1931 is configured to allow insertion of the first and second bone pins 610, 620 therethrough and through the first and second scaffold holes 220, 230 in the base scaffold 200 to secure the base scaffold 200 and the first ray alignment guide 1905 to the first metatarsal 600 while facilitating translation of the first ray alignment guide 1905 relative to the base scaffold 200, generally along the scaffold axis 202 and the alignment axis 1902. The first ray alignment guide 1905 also includes a rack slot 1932 that is configured to receive therethrough a distal end of a cam axle 2020 of the compressor-distractor 2000 in the assembled configuration. The distal end of the cam axle 2020 is preferably inserted into and through the axle hole 260 of the base scaffold 200 in the assembled configuration and is held in the axle hole 260 by the retaining clip 950. The cut aperture 740 is configured to removably attach the cuneiform cut guide 800 utilizing the supports 750 positioned within the cut aperture 740 and configured to receive corresponding positioning guides 810 of the cuneiform cut guide 800. First and second cuneiform holes 760, 761 are preferably oriented parallel to each other and perpendicular to the top surface 1930 and are configured to accept the first and second cuneiform bone pins 1110, 1120 for securing the first ray alignment guide 1905 to the medial cuneiform. First and second angled holes 770, 771 are configured to accept one or more of the third cuneiform bone pins 1130 with an axis oblique to the axes of first and second angled cuneiform holes 760, 761, thereby defining an acute angle □ between the first and second angled holes 770, 771 and the first and second cuneiform holes 760, 761. The rack slot 1932 includes teeth 1980 extending inwardly toward a center of the rack slot 1932 that are configured to engage with a pinion 2040 proximate a distal end of the compressor-distractor body 2010 in the assembled configuration. The teeth 1980 and the pinion 2040 are preferably configured to facilitate translation of the base scaffold 200 generally parallel to the scaffold axis 202 and the alignment axis 1902 of the first ray alignment guide 1900 in reactance to a force applied to compressor-distractor pinion 2040 by rotating the compressor-distractor body 2010. When the first ray multi-tool 2100 is attached to the metatarsal 600 and the medial cuneiform 1140, the compressor-distractor assembly 2000 is configured to drive movement of the first metatarsal 600 relative to the medial cuneiform 1140, generally parallel to the scaffold axis 202 and the alignment axis 1902. In a preferred operation of the first ray multi-tool 2100 of the fifth preferred embodiment, a counterclockwise torque applied to compressor-distractor body 2010 by rotating the cam lever handle 921 of compressor-distractor assembly 2000 about a longitudinal axis of the cam axle 2020 results in a force translation from the pinion 2040 to the teeth 1980 creating motion of the base scaffold 200 and attached first metatarsal 600 away from the TMT joint causing joint distraction when the cuneiform side 706 is attached to the medial cuneiform 1140, while a clockwise torque applied to the compressor-distractor body 2010 by rotating the cam lever handle 921 of the compressor-distractor assembly 2000 with the cam lever handle 921 results in motion of the base scaffold 200 and attached first metatarsal 600 toward the TMT joint causing joint compression when the cuneiform side 706 is attached to the medial cuneiform 1140.

In the fifth preferred embodiment, the compressor-distractor assembly 2000 includes the compressor-distractor body 2010 that is configured to receive the cam axle 2020. The cam lever 920 includes the cam lever handle 921 that is configured to attach to the cam axle 2020 by the cam lever center 930. The cam lever center 930 is rotatably positioned in the cam lever center hole 923 with the cam lever center axis 931 aligned with the cam lever center hole axis 924. The cam lever center 930 is configured to receive a cam head 2020*a* of the cam axle 2020 through a hole perpendicular to the cam lever center axis 931 such that the cam head 2020*a* of the cam axle 2020 does not pass through the cam lever center 930. The cam lever 920 includes the cam lever edge 922 having the cam-shaped circumference around the cam lever center axis 924. The retaining clip 950 is secured to the distal end of the cam axle 2020 in a groove 2030 to retain the cam axle 2020 relative to the base scaffold 200, the first ray alignment guide 1905, and the compressor-distractor body 2010. In the assembled configuration, the cam axle 2020 is placed through the cam lever 920, cam lever center 930, compressor-distractor body 2010, the rack slot 1932 and axle hole 260 of the base scaffold 200. The first ray alignment guide 1905 is slidably attached to the metatarsal base scaffold 200. The retaining clip 950 is secured onto the groove 2030, thereby securing the compressor-distractor assembly 2000 to the first ray alignment guide 1900 and metatarsal base scaffold 200.

In operation, a torque applied to cam lever handle 921 of the fifth preferred embodiment about the longitudinal axis of the cam axle 2020 imparts a rotation of the compressor-distractor body 2010 and the attached pinion 2040 thereby causing the pinion 2040 to impart a force directed along the alignment axis 1902 of the first ray alignment guide 1905 against the teeth 1980 and relative to an equal and opposite force applied to the base scaffold 200 through hole 260. In a further aspect of operation of the fifth preferred embodiment, rotation of cam lever handle 921 about the cam lever center 930 to a position such that the longitudinal axis of the cam lever handle 921 is generally parallel to the cam axle 2020 or oriented generally vertically imparts a force created by the cam lever edge 922 on the compressor-distractor body 2010 thereby imparting an upward directed force through the cam axle 940 to the retaining clip 950. The upward force one the retaining clip 950 is directed upon the metatarsal base scaffold 200 and is countered by an equal and downward force imparted by the compressor-distractor body 2010 directed upon the top surface 730 of the first ray alignment guide 1905. The forces between the base scaffold 200 and the first ray alignment guide 1905 applied through the retaining clip 950, the cam axle 2020 and the cam lever 920 of the fifth preferred embodiment create a frictional force generally preventing translational motion between the base scaffold 200 and the first ray alignment guide 1900 thereby locking the position of the first metatarsal 600 relative to the medial cuneiform 1140 for subsequent fixation or manipulation relative to other anatomical structures, such as the second metatarsal 1100.

The fifth preferred first ray multi-tool 2100 with base scaffold 200, the first ray alignment guide 1905, and the attached compressor-distractor cam assembly 2000 is similar in function and operation to the first ray multi-tool 1000 of the third preferred embodiment, the first ray multi-tool 1700 of the alternative third preferred embodiment and the first ray multi-tool 1800 of the fourth preferred embodiment and may be utilized with the other components described herein during a procedure, such as the first preferred cut guide 100, the assembled base scaffold 200 and the metatarsal cut guide 300 and the cuneiform cut guide 800. The fifth preferred first ray multi-tool 2100 is provided to the user pre-assembled in an instrument kit and is preferably sterile packaged such that the user is able to remove from the sterile package and utilize the fifth preferred first ray multi-tool 2100 for a procedure, which is also preferred for all of the additional components described herein, including the first preferred cut guide 100, the assembled base scaffold 200 and metatarsal cut guide 300, the first ray multi-tool 100 of the second preferred embodiment, the first ray multi-tool 1700 of the alternative third preferred embodiment, the first ray multi-tool 1000 of the third preferred embodiment, and the first ray multi-tool 1800 of the fourth preferred embodiment. The individual components of the preferred embodiments described herein may alternatively be provided to the user as removably attachable separate components of an instrument kit for assembly by the user prior to use. Alternative preferred embodiments are also contemplated whereby any two or more of the individual components of the preferred embodiments may be partially or fully assembled in sterile packaging, removably from the packaging and provided to the user in an instrument kit.

Referring to FIGS. 22*a*-24*c*, a preferred cut guide insert 2200 that may be utilized with any of the preferred cut guides 100, 300, 800 described herein includes a cut body 2210 with a top edge 2220*a* and a bottom edge 2220*b*, a first side support 2222*a*, a second side support 2222*b*, a first grasping arm 2230*a* extending from the first side support 2222*a* and a second grasping arm 2230*b* extending from the second side support 2222*b*. The cut body 2210 extends generally a length of cut guide insert 2200 between the first and second side supports 2222*a*, 2222*b* and the top and bottom edges 2220*a*, 2220*b*. The cut guide insert 2200 is configured to be removably inserted into the multi-tool slot 170, 370 or cut guide slot 840 of the preferred cut guides 100, 300, 800. The first and second side supports 2222*a*, 2222*b* define first and second rims 2221*a*, 2221*b* adjacent a slot side 2210*a* of the cut body 2210. The cut body 2210, the top and bottom edges 2220*a*, 2220*b*, and the first and second rims 2221*a*, 2221*b* define a cut slot 2224 into which the cutting blade 1900 of a bone saw may be inserted for cutting a bone or bone surface for preparation of the bone or bone surface for further procedures, such as by forming the metatarsal cut plane 600*c* or the cuneiform cut plane 1140*b*. The first and second grasping arms 2230*a*, 2230*b* preferably extend from the first and second side supports 2222*a*, 2222*b* of the cut body 2210, respectively, and are configured to allow handling, removal, and insertion of the cut guide insert 2200 into and out of the multi-tool slots 170, 370 and/or the cut guide slot 840.

The preferred cut guide insert 2200 includes a central or reference axis 2240 centered and perpendicular to the cut body 2210 and a longitudinal axis 2250 aligned generally parallel with the cut body 2210. The cut slot 2224 is proximate to longitudinal axis 2250 and spans the length of the cut body 2210 between the top and bottom edges 2220*a*, 2220*b* and the first and second rims 2221*a*, 2221*b*. The cut guide insert 2200 may be utilized with the first preferred cut guide 100 by aligning the cut body 2210 with the multi-tool slot 170. The cut guide insert 2200 is configured to be removably inserted into multi-tool slot 170 from above such that the cut slot 2224 may be oriented proximate to the positioner 160 or distant relative to the positioner 160 by pivoting the cut guide insert 2200 one hundred eighty degrees (180°) relative to the multi-tool slot 170.

The cut guide insert 2200 may be positioned within the multi-tool slot 170, 370 or the cut guide slot 840 of the first preferred cut guide 100, the assembled base scaffold 200 and the metatarsal cut guide 300, the cuneiform cut guide 800 or nearly any component that includes a slot for alignment and cutting with the cutting blade 1900 to align the cutting blade 1900. A first cut distance $d_{1C}$ is defined by as space between the positioner 160 and the cut slot 2224 when the cut guide insert 2200 is positioned within the multi-tool slot 170 in a first orientation with the cut slot 2224 proximate to the positioner 160. A second cut distance $d_{2C}$ is defined by a space between the positioner 160 and the cut slot 2224 when the cut guide insert 2200 is positioned within multi-tool slot 170 in a second orientation such that the cut slot 2224 is distant to the positioner 160, wherein the second cut distance $d_{2C}$ is greater than the first cut distance $d_{1C}$ and the cut guide insert 2200 is pivoted one hundred eighty degrees (180°) relative to the multi-tool slot 170 between the first and second orientations.

In an exemplary operation of the preferred embodiment, the first preferred cut guide 100 is attached to the dorsal aspect of a first metatarsal 600 with bone pins, such as the first and second metatarsal bone pins 620, 620, such that the first cut guide axis 100*a* of the first preferred cut guide 100 is generally aligned with the first metatarsal axis 600*a* of the metatarsal 600 and with the positioner 160 abutting the articular surface of the first metatarsal base 600*b*. A bone saw with the cutting blade 1900 is inserted through cut slot 2224 with the cut guide insert 2200 in the first orientation to remove a first bone portion of the first cut distance $d_{1C}$. If it is determined by the medical professional that additional bone is to be removed, the cut guide insert 2200 is removed from the multi-tool slot 170 without detaching the first preferred cut guide 100 from the first metatarsal 600 and re-inserted in the second orientation. The cutting blade 1900 of the bone saw is inserted through cut slot 2224 to remove a second bone portion of the second cut distance $d_{2C}$.

Referring to FIGS. 25-30, a first ray multi-tool 2500 in accordance with a sixth preferred embodiment may be mounted to the first metatarsal 600 with a bone pin 2530. The first ray multi-tool 2500 of the sixth preferred embodiment has similar features relative to the first ray multi-tools 1000, 1700, 1800, 2100 of the third, third alternative, fourth and fifth preferred embodiments and is shown with the same reference numbers utilized to identify similar features and the differences between the third, third alternative, fourth, and fifth preferred embodiments and the sixth preferred embodiment are described below with different reference numbers utilized to identify the different features of the sixth preferred embodiment of the first ray multi-tool 2500. The first ray multi-tool 2500 is configured such that the bone pin 2530 protrudes through the arcuate slot 2520 that extends through a compressor-distractor cam 2510 of a compressor-distractor assembly 2505 and contacts the cam surface 2510*a* to urge generally translational movement between the base scaffold 2550 and the first ray alignment guide 2540. The arcuate slot 2520 defines a cam surface 2510*a*. A metatarsal base scaffold 2550 is movably attached to a first ray alignment guide 2540 such that the metatarsal base scaffold 2550 is capable of rotation generally about a first metatarsal axis 600*a* of the first metatarsal 600 and translation along an alignment axis 2540*a* of the first ray alignment guide 2540 and whereby the motion of the base scaffold 2550 is relative to the first ray alignment guide 2540.

The first ray alignment guide 2540 of the sixth preferred embodiment includes the angled cuneiform hole 770 on the cuneiform side 706 and an angled metatarsal aperture 2720 on the metatarsal side 704. The angled cuneiform hole 770 is preferably oriented at a cuneiform acute angle C relative to the first cuneiform hole 760 and the angled metatarsal aperture 2720 is preferably oriented at a metatarsal acute angle D relative to the first metatarsal aperture 2730. The orientations of the angled cuneiform hole 770, the angled metatarsal aperture 2720, the first cuneiform hole 760 and the first metatarsal aperture 2730 preferably direct the bone pins, K-wires or other fasteners that are inserted into the holes or apertures 770, 2720, 760, 2730 generally toward and through the first metatarsal axis 600*a* and the center of the medial cuneiform 1140, respectively.

The sixth preferred first ray multi-tool 2500 includes the base scaffold 2550, a rotation insert 2600, the first ray alignment guide 2540 and the compressor-distractor assembly 2505. The first ray multi-tool 2500 is preferably delivered assembled in a sterile package as a kit for correction of mis-alignment of bones across a joint or bone segments and for compression and/or distraction of the bones or bone segments. The sixth preferred first ray multi-tool 2500 is not limited to being delivered in the sterile package or being delivered in an assembled configuration and may be otherwise delivered as components for assembly by the user. The individual components of the first ray multi-tool 2500 are preferably constructed of a biocompatible polymeric material that is relatively stiff and strong, is able to take on the general size and shape of the individual components, is able to withstand the normal operating conditions of the components and is able to perform the functions of the components of the first ray multi-tool 2500. The components of the other preferred first ray multi-tools 1000, 1700, 1800, 2100 are also preferably constructed of the biocompatible polymeric material and are similarly packaged but are not so limited and may be individually supplies and may be constructed of nearly any biocompatible, strong and stiff structural material, such as metals or other materials that are often utilized for construction of medical devices and instruments.

The base scaffold 2550 of the sixth preferred embodiment includes a bone-contacting surface 2551, a generally box-shaped scaffold body 2552, and an arcuate-shaped scaffold plate 2553 secured to a top of the scaffold body 2552 and extending at a cantilever from a distal side of the scaffold body 2552. The base scaffold 2550 also includes first and second scaffold holes 2552*a*, 2552*b* extending through the scaffold body 2552, the scaffold plate 2553 and the bone-contacting surface 2551 and a scaffold slot 2610 extending through the scaffold plate 2553 in the portion that cantilevers from the scaffold body 2552. The scaffold slot 2610 is preferably elongate along the scaffold axis 202.

The rotation insert 2600 of the sixth preferred embodiment includes an actuation block 2601 at a distal end having a top surface 2601*a* and a bottom bridge 2601*b*, a proximal body 2603, and first and second side rails 2602*a*, 2602*b* that extend between the actuation block 2601 and the proximal body 2603. The rotation insert 2600 is configured for mounting between the base scaffold 2550 and the first ray alignment guide 2540 in the mounted configuration. A pivot guide slot 2604 is defined by the actuation block 2601, upper surfaces of the first and second side rails 2602*a*, 2602*b* proximate the actuation block 2601 and the bottom bridge 2601*b*. The bottom bridge 2601*b* preferably includes a bridge hole 2605 therethrough that is aligned with the cam axle hole 2620 in the assembled configuration. The pivot guide slot 2604 is configured to accept the scaffold plate 2553 therein in the assembled configuration to facilitate translation of the base scaffold 2550 relative to the rotation insert 2600, as well as pivoting of the rotation insert 2600 relative to the base scaffold 2550. In the assembled configuration, the first and second side rails 2601 engage sides of the base scaffold 2550 to further guide the translational movement of the rotation insert 2600 relative to the base scaffold 2550. A distal end of an arcuate arm 2701 of the first ray alignment guide 2540 also extends into pivot guide slot 2604 but only into a portion between a proximal side 2601c of the actuation block 2601 and a distal wall 2601d of the actuation block 2601 in the assembled configuration. In contrast, the distal end of the scaffold plate 2553 extends into and through the distal portion of the pivot guide slot 2604 that extends through the distal wall 2601d. An opening portion of the pivot guide slot 2604 that opens through the distal wall 2601d generally prevents pivoting movement of the base scaffold 2550 relative to the rotation insert 2600 but the pivot guide slot 2604 accommodates pivoting movement of the first ray alignment guide 2540 relative to the base scaffold 2550 and the rotation insert 2600, at least partially because the arcuate arm 2701 of the first ray alignment guide 2540 does not extend through the opening portion of the pivot guide slot 2604 but only into the pivot guide slot 2604 between the bottom bridge 2601b, the first and second side rails 2602a, 2602b and an underside of the actuation block 2601 in the assembled configuration, as the pivot guide slot 2604 includes side openings 2604a at both sides proximally relative to the distal wall 2601d. The base scaffold is slidably attached to the rotation insert 2600 such that the base scaffold 2550 is capable of motion only along the scaffold axis 202 or a longitudinal axis of the rotation insert 2600. The scaffold slot 2610 of the base scaffold 2550 is aligned with the cam axle hole 2620 that extends through the actuation block 2601 and the bottom bridge 2601b such that the distal end of the cam axle 940 may be inserted through the cam axle hole 2620 and the scaffold slot 2610 in the assembled configuration and this generally does not impede the translational motion of base scaffold 2550 relative to the rotation insert 2600 except for translation limits resulting if the cam axle 940 contacts proximal and distal ends of the scaffold slot 2610.

The first ray alignment guide 2540 of the sixth preferred embodiment includes the cuneiform side 706 and the cut aperture 740 having similar or the same features as the cuneiform sides 706 and the cut apertures 740 of the third, alternative third, fourth and fifth preferred embodiments of the first ray alignment guides 700, 1820, 1905 of the first ray multi-tools 1000, 1700, 1800, 2100. The arcuate arm 2701 of the first ray alignment guide 2540 extends from the cut aperture 740 to a distal guide end 2701a and has a generally arcuate shape with a top surface 2701b and a lower surface 2701c. In the assembled configuration, the distal guide end 2701a is typically positioned in the proximal portion of the pivot guide slot 2604 proximal relative to the distal wall 2601d and distal relative to the proximal side 2601c of the actuation block 2601. The translation and pivoting movements of the first ray alignment guide 2504 relative to the base scaffold 2550 and the rotation insert 2600 are guided by upper surfaces of the base scaffold 2550 and the first and second side rails 2602a, 2602b against the lower surface 2701c of the first ray alignment guide 2504 and the underside of the actuation block 2601 in the pivot guide slot 2604 against the top surface 2701b of the arcuate arm 2701. The first ray alignment guide 2540 also includes a first metatarsal aperture 2730 preferably having a first side 2730a and a second side 2730b, a second metatarsal aperture 2732, which is comprised of a hole in the sixth preferred embodiment, and a metatarsal angled aperture 2720. The angled aperture 2720 is preferably angled relative to the orientation of the first metatarsal aperture 2730 such that fasteners, K-wires or bone pins that are inserted through the first metatarsal aperture 2730 and the angled aperture 2720 are generally directed toward a center of the bone, such as the first metatarsal 600 and the metatarsal axis 600a.

The compressor-distractor assembly 2505 of the sixth preferred embodiment includes the compressor-distractor cam 2510 with the cam axle hole 911 that is configured to receive the cam axle 940 about which the compressor-distractor cam 2510 rotates in operation. The cam lever 920 having the cam lever handle 921 is configured to attach to the cam axle head 940a of the cam axle 940 through the cam lever center 930. The cam lever center 930 is rotatably positioned in the cam lever center hole 923 of the cam lever 920 with the cam lever center axis 931 aligned with the cam lever center hole axis 924. The cam lever center 930 is configured to receive the cam axle 940 and the cam axle head 940a through a hole perpendicular to the cam lever center axis 931 such that the cam axle head 940a of the cam axle 940 cannot pass through the cam lever center 930. The cam lever 920 includes the cam lever edge 922 having a cam-shaped circumference around the cam lever center axis 924. A retaining clip 950 is secured to the distal end of the cam axle 940 in the groove 941. In the assembled configuration, the cam axle 940 is placed through the cam lever 920, the cam lever center 930, the cam axle hole 911, the cam axle hole 2620 in the actuation block 2601, the second metatarsal aperture 2732 in the arcuate arm 2701 of the first ray alignment guide 2540, the scaffold slot 2610 in the base scaffold 2550 and the bridge hole 2605 in the bottom bridge 2601b of the actuation block 2601. The laterally oblong configuration of the second metatarsal aperture 2732 of the arcuate arm 2701 of the first ray alignment guide 2540 facilitates rotational movement of the first ray alignment guide 2540 relative to the rotation insert 2600 and the base scaffold 2550. The base scaffold 2550 is slidably attached to the rotation insert 2600, such that the base scaffold 2550 is translatable relative to the rotation insert 2600. The retaining clip 950 is secured onto the groove 941 thereby securing the compressor-distractor assembly 2505 to the first ray alignment guide 2540 and base scaffold 2550.

In operation, the first ray multi-tool 2500 of the sixth preferred embodiment is removed from the sterile package for the procedure and the TMT joint is prepared with the tools and instruments described herein. The base scaffold 2550 is secured to the first metatarsal 600 with first, second and/or third metatarsal bone pins 610, 620, 630, 2530 to secure the first ray multi-tool 2500 to the first metatarsal 600. The cuneiform side 706 is secured to the medial cuneiform 1140 with first, second and/or third cuneiform bone pins 1110, 1120, 1130 with the cut aperture 740 generally positioned above the TMT joint, and the alignment axis 702 aligned generally parallel to the first metatarsal axis 600a. A torque is applied to cam lever handle 921 about the cam axle 940 with the cam lever handle 921 generally in the horizontal orientation, which imparts a rotation of the compressor-distractor cam 2510. The rotation of the compressor-distractor cam 2510 causes the cam surface 2510a of the arcuate cam slot 2520 to impart a force on bone pin 2530 directed along the alignment axis 702 of the first ray alignment guide 2540. The bone pin 2530 therein imparts the translational force on the base scaffold 2550 relative to an equal and opposite force applied by the cam axle 940 onto the first metatarsal aperture 2730. The medial cuneiform 1140 and the first metatarsal 600 may be compressed or distracted depending on the direction that the compressor-distractor 2510 is rotated.

In a further aspect of operation of the sixth preferred embodiment, rotation of cam lever 920, preferably utilizing the cam lever handle 921, about the cam lever center 930 to a position such that the cam lever handle 921 is oriented generally vertically or generally parallel to a longitudinal axis of the cam axle 940 imparts a force created by the cam edge 922 on the compressor-distractor cam 2510 thereby imparting an upward directed force through the cam axle 940 to the retaining clip 950 against a bottom surface of the bottom bridge 2601b. The upward force of the retaining clip 950 on the bottom bridge 2601b applies a squeezing or compression force on the scaffold plate 2553, the arcuate arm 2701, the actuation block 2601 and the bottom portion of the compressor-distractor cam 2510 adjacent the exit of the cam axle hole 911 out of the bottom of the compressor-distractor cam 2510. The forces between the rotation insert 2600, the base scaffold 2550 and the first ray alignment guide 2540 creates a frictional force generally preventing translational and rotational motion between the metatarsal base scaffold 2550 and the first ray alignment guide 2540 when the cam lever 920 is oriented in the locking position. The compression forces resulting from orienting the cam lever 920 in the locking position results in deformation of the bridge bottom bridge 2601b and other components under compression force, as the components are constructed of the biocompatible polymeric material. In the preferred embodiment, the construct combining the metatarsal base scaffold 2550, the first ray alignment guide 2540, the rotation insert 2600, and the attached compressor-distractor slot cam assembly 2505 is considered an equivalent functional tool to herein described preferred embodiments of the first ray multi-tool 1000, 1700, 1800, 2100 and is preferably provided to the user pre-assembled in an instrument kit in a sterile package.

Referring to FIGS. 25-27 and 31, an alternative sixth preferred first ray alignment guide 2740 includes many of the same or similar features as the sixth preferred first ray alignment guide 2540 and may be substituted in the sixth preferred first ray multi-tool 2500 of the sixth preferred embodiment and utilized in the same or similar procedures. The sixth and alternative preferred sixth preferred first ray alignment guides 2540, 2740 have the same or similar features with the alternative sixth preferred first ray alignment guide 2740 also including an integrally formed alignment outrigger 2742 with an alignment leg 2744 extending substantially parallel to the alignment axis 702 and spaced laterally from the alignment axis 702. The first ray alignment guide 2740 of the additional sixth preferred embodiment is similarly designed and configured as the sixth preferred first ray alignment guide 1540 and the same reference numbers are utilized to identify the same or similar features of the alternative sixth preferred first ray alignment guide 2740 relative to the sixth preferred first ray alignment guide 1540. The alignment outrigger 2742 and the alignment leg 2744 are configured and operate similarly or substantially the same as the alignment outrigger 820 and the alignment leg 822 of the second preferred embodiment, but the alignment outrigger 2742 and alignment leg 2744 are integrally formed with the first ray alignment guide 2740. The alternative sixth preferred first ray alignment guide 2740 may be delivered to the user individually for assembly or may be provided in the kit pre-assembled with other components, such as the base scaffold 2550, the rotation insert 2600 and the compressor-distractor assembly 2505 of the sixth preferred embodiment, or other components or assemblies of the first ray multi-tools described herein or with other components as would be apparent to one having ordinary skill in the art based on reviewing the present disclosure. The It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A kit for adjusting a first metatarsal of a patient relative to a medial cuneiform, the kit comprising:
   a base scaffold having a scaffold axis, a top surface, a first scaffold hole extending through the base scaffold and the top surface, and a guide surface;
   a first ray alignment guide, the first ray alignment guide including an alignment axis, a metatarsal side, a cuneiform side, and a cut aperture between the metatarsal side and the cuneiform side, the cuneiform side including a first cuneiform hole extending therethrough, the metatarsal side including a first metatarsal aperture extending therethrough and a first rail, the metatarsal side integrally formed with the cuneiform side, the first ray alignment guide movably mountable to the base scaffold with the guide surface and the first rail capable of guiding movement of the first ray alignment guide relative to the base scaffold generally parallel relative to the scaffold axis in a mounted configuration, the first scaffold hole alignable with the first metatarsal aperture in the mounted configuration;
   a first bone pin configured for connection to the first metatarsal and extension through the first scaffold hole and the first metatarsal aperture in the mounted configuration; and
   a second bone pin configured for connection to the medial cuneiform and extension through the first cuneiform hole, the base scaffold and first ray alignment guide facilitating alignment of the first metatarsal and the medial cuneiform and compression or distraction of the first metatarsal relative to the medial cuneiform in the mounted configuration.

2. The kit of claim 1, further comprising:
   a cut guide configured for removable mounting to the first ray alignment guide at the cut aperture, the cut guide including a body, a cut guide slot and an alignment outrigger, the alignment outrigger including an alignment leg, the cut guide slot oriented substantially perpendicular to the alignment leg.

3. The kit of claim 2, wherein the cut guide includes a positioning guide extending from the body and the first ray alignment guide includes supports in the aperture, the positioning guide capable of interacting with the supports to connect the cut guide to the first ray alignment guide when the cut guide is mounted to the first ray alignment guide.

4. The kit of claim 2, wherein the cut guide includes a positioner proximate and generally parallel to the cut guide slot and configured for placement into a joint between the first metatarsal and the medial cuneiform, the positioner configured to aid in orienting the cut slot for cutting a medial cuneiform head of the medial cuneiform.

5. The kit of claim 1, wherein the first ray alignment guide includes an alignment outrigger having an alignment leg, the alignment leg defining an alignment leg axis, the alignment leg axis spaced from and oriented generally parallel to the alignment axis.

6. The kit of claim 1, wherein the first ray alignment guide includes an angled cuneiform hole and an angled metatarsal aperture, the angled cuneiform hole oriented at a cuneiform acute angle relative to the first cuneiform hole, the angled metatarsal aperture oriented at a metatarsal acute angle relative to the first metatarsal aperture.

7. The kit of claim 1 further comprising:
a compressor-distractor assembly including a compressor-distractor cam with a cam axle hole, a cam axle and a cam lever, the compressor-distractor assembly removably mountable to the first ray alignment guide such that the cam axle hole is alignable with a second metatarsal aperture.

8. The kit of claim 7, wherein the cam axle extends through the cam axle hole and into the second metatarsal aperture, the cam axle configured to lock the base scaffold to the first ray alignment guide when the cam lever is in a locked configuration.

9. The kit of claim 1, wherein the metatarsal side and the cuneiform side are aligned along the alignment axis and are connected across the cut aperture by an aperture leg.

10. The kit of claim 1, further comprising:
a rotation insert configured for mounting between the base scaffold and the first ray alignment guide in the mounted configuration.

11. A kit for adjusting a first metatarsal having a first metatarsal axis relative to a medial cuneiform, the kit comprising:
a base scaffold having a scaffold axis, a top surface, and a first scaffold hole extending through the base scaffold and the top surface;
a cut guide including a body, a cut guide slot, cut guide axis and a positioner, the cut guide configured for removable mounting to the first metatarsal such that the cut guide axis is oriented generally parallel to the first metatarsal axis, the cut guide slot and the positioner oriented generally perpendicular to the cut guide axis;
a first ray alignment guide having an alignment axis, a metatarsal side, a cuneiform side, a cut aperture between the metatarsal side and the cuneiform side, a first metatarsal aperture and a first cuneiform hole, the first ray alignment guide configured for removable mounting to the first metatarsal and the medial cuneiform;
a compressor-distractor assembly including a compressor-distractor cam having a cam slot, a cam axle movably mounted in the cam slot and a cam lever, the cam axle extending through the first metatarsal aperture; and
a first fastener configured to extend through the first scaffold hole to secure the base scaffold to the first metatarsal, the scaffold axis oriented generally parallel to the first metatarsal when the base scaffold is secured to the first metatarsal.

12. The kit of claim 11, further comprising:
an attachment knob including a threaded shaft and a head, the cut guide includes a cut guide arm that defines the cut guide axis, the cut guide arm including an anchor hole, the threaded shaft capable of extending through the anchor hole to secure the cut guide to the base scaffold by engagement between the threaded shaft and the first scaffold hole.

13. The kit of claim 11, wherein the metatarsal side includes a first rail and the first metatarsal aperture, the cuneiform side including the first cuneiform hole and a first angled cuneiform hole, the first ray alignment guide movably mountable to the base scaffold through interaction between a guide surface of the base scaffold and the first rail such that the first ray alignment guide is slidable generally parallel relative to the scaffold axis in a mounted configuration.

14. The kit of claim 11, wherein the compressor-distractor cam includes a top cam surface, a bottom cam surface and an arcuate cam slot extending through the compressor-distractor cam between the top cam surface and the bottom cam surface, the first fastener configured to extend through the arcuate cam slot when the base scaffold, the first ray alignment guide and the compressor-distractor assembly are mounted to the first metatarsal.

15. The kit of claim 11, further comprising:
a rotation insert capable of being mounted between the base scaffold and the first ray alignment guide in a mounted configuration.

16. The kit of claim 11, further comprising:
a cuneiform cut guide having a positioning guide, a cut guide slot, a cuneiform positioner and an alignment outrigger with an alignment leg, the cut guide slot oriented substantially perpendicular to the alignment leg, the positioning guide configured for removable mounting to the first ray alignment guide at the cut aperture.

17. The kit of claim 11, wherein the cut guide is integrally formed with the base scaffold.

18. The kit of claim 11, wherein the base scaffold includes a second base aperture extending through the base scaffold and the top surface and the kit comprises a second fastener capable of extending through the second base aperture to secure the base scaffold to the first metatarsal.

19. The kit of claim 11, wherein: the base scaffold includes an angled scaffold hole, the angled scaffold hole oriented at an angle relative to the first scaffold hole.

* * * * *